(12) United States Patent
Weber et al.

(10) Patent No.: US 7,625,888 B2
(45) Date of Patent: Dec. 1, 2009

(54) FUSED TRIAZOLE DERIVATIVES AS DIPEPTIDYL PEPTIDASE-IV INHIBITORS FOR THE TREATMENT OR PREVENTION OF DIABETES

(75) Inventors: Ann E. Weber, Scotch Plains, NJ (US); Wallace T. Ashton, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 519 days.

(21) Appl. No.: 11/660,130

(22) PCT Filed: Aug. 19, 2005

(86) PCT No.: PCT/US2005/029591

§ 371 (c)(1),
(2), (4) Date: Feb. 13, 2007

(87) PCT Pub. No.: WO2006/023750

PCT Pub. Date: Mar. 2, 2006

(65) Prior Publication Data

US 2007/0208010 A1    Sep. 6, 2007

Related U.S. Application Data

(60) Provisional application No. 60/603,727, filed on Aug. 23, 2004.

(51) Int. Cl.
| | | |
|---|---|---|
| *C07D 471/00* | (2006.01) | |
| *C07D 487/00* | (2006.01) | |
| *A61K 31/44* | (2006.01) | |
| *A61K 31/495* | (2006.01) | |
| *A61K 31/55* | (2006.01) | |
| *A61P 3/00* | (2006.01) | |

(52) U.S. Cl. .......................... 514/211.11; 514/214.02; 514/220; 514/250; 514/257; 514/293; 540/548; 540/562; 540/586; 544/251; 544/346; 546/82

(58) Field of Classification Search ............ 514/211.11, 514/214.02, 220, 250, 257, 293; 540/548, 540/562, 586; 544/251, 346; 546/82
See application file for complete search history.

(56) References Cited

FOREIGN PATENT DOCUMENTS

| WO | WO 97/03986 | 2/1997 |
|---|---|---|
| WO | WO 02/076450 A1 | 10/2002 |
| WO | WO 03/000180 A2 | 1/2003 |
| WO | WO 03/000181 A2 | 1/2003 |
| WO | WO 03/004498 A1 | 1/2003 |
| WO | WO 03/082817 A2 | 10/2003 |
| WO | WO 2004/007468 A1 | 1/2004 |
| WO | WO 2004/032836 A2 | 4/2004 |
| WO | WO 2004/037169 A2 | 5/2004 |
| WO | WO 2004/043940 A1 | 5/2004 |
| WO | WO 2004/050022 A2 | 6/2004 |
| WO | WO 2004/058266 A1 | 7/2004 |
| WO | WO 2004/064778 A2 | 8/2004 |
| WO | WO 2004/069162 A2 | 8/2004 |
| WO | WO 2004/110436 A1 | 12/2004 |
| WO | WO 2004/112701 A2 | 12/2004 |
| WO | WO 2005/011581 A2 | 2/2005 |
| WO | WO 2005/044195 A2 | 5/2005 |
| WO | WO 2005/108382 A1 | 11/2005 |
| WO | WO 2005/116029 A1 | 12/2005 |
| WO | WO 2006/066747 A1 | 6/2006 |
| WO | WO 2006/066770 A1 | 6/2006 |

OTHER PUBLICATIONS

Demuth, H.U. et al., "Type 2 diabetes—Therapy with dipeptidyl peptidase IV inhibitors" Biochimica et Biophysica Acta, vol. 1751, pp. 33-44, 2005.
Holst, J. J., "Treatment of Type 2 diabetes mellitus with agonists of the GLP-1 receptor or DPP-IV inhibitors" Expert Opin. Emerg. Drugs, vol. 9, No. 1, pp. 155-166, 2004.
Deacon, C. F. et al., "Inhibitors of dipeptidyl peptidase IV: a novel approach for the prevention and treatment of Type 2 diabetes?", Expert Opin. Investig. Drugs, vol. 13, No. 9, pp. 1091-1102, 2004.
Augustyns, K. et al., "Dipeptidyl peptidase IV inhibitors as new therapeutic agents for the treatment of Type 2 diabetes", Expert Opin. Ther. Patents, vol. 13, No. 4, pp. 499-510, 2003.
"Novel N. substituted-2-cyanopyrrolidines as potent inhibitors of dipeptidyl peptidase IV in the treatment of non-insulin-dependent diabetes mellitus" Exp. Opin. Ther. Patents, vol. 10, No. 12, pp. 1937-1942, 2000.
Drucker, D. J., "Therapeutic potential of dipeptidyl peptidase IV inhibitors for the treatment of type 2 diabetes" Expert Opin. Investig. Drugs, vol. 12, No. 1, pp. 87-100, 2003.
Vahl, T. P. et al., "Gut peptides in the treatment of diabetes mellitus" Expert Opin. Investig. Drugs, vol. 13, No. 3, pp. 177-188, 2004.
Weber, A. E., "Dipeptidyl Peptidase IV Inhibitors for the Treatment of Diabetes" J. Med. Chem., vol. 47, pp. 4135-4141, 2004.
Holst, J. J. et al., "Glucagon-like peptide 1 and inhibitors of dipeptidyl peptidase IV in the treatment of type 2 diabetes mellitus" Current Opinion in Pharmacology, vol. 4, pp. 589-596, 2004.
Deacon, C. F., "Perspectives in Diabetes—Therapeutic Strategies Based on Glucagon-Like Peptide 1" Diabetes, vol. 53, pp. 2181-2189, 2004.
Augustyns, K. et al., "Inhibitors of proline-specific dipeptidyl peptidases: DPP IV inhibitors as a novel approach for the treatment of Type 2 diabetes" Expert Opin. Ther. Patents, vol. 15, No. 10, pp. 1387-1407, 2005.

(Continued)

*Primary Examiner*—Bruck Kifle
(74) *Attorney, Agent, or Firm*—Philippe L. Durette; Catherine D. Fitch

(57) ABSTRACT

The present invention is directed to novel fused triazole derivatives which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

22 Claims, No Drawings

FUSED TRIAZOLE DERIVATIVES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2005/029591, filed 19, Aug. 2005, which claims the benefit under 35 U.S.C. 119(e) of U.S. Provisional Application No. 60/603,727, filed 23, Aug. 2004.

FIELD OF THE INVENTION

The present invention relates to novel fused triazole derivatives which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (IDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV") enzyme are also under investigation as drugs that may be useful in the treatment of diabetes, and particularly Type 2 diabetes. See for example WO 97/40832, WO 98/19998, U.S. Pat. No. 5,939,560, *Bioorg. Med. Chem. Lett.*, 6: 1163-1166 (1996); and *Bioorg. Med. Chem. Lett.*, 6: 2745-2748 (1996). The usefulness of DPP-IV inhibitors in the treatment of Type 2 diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively to date, especially for utilities other than diabetes. New compounds are needed so that improved DPP-IV inhibitors can be found for the treatment of diabetes and potentially other diseases and conditions. The therapeutic potential of DPP-IV inhibitors for the treatment of Type 2 diabetes is discussed by D. J. Drucker in *Exp. Opin. Invest. Drugs*, 12: 87-100 (2003) and by K. Augustyns, et al., in *Exp. Opin. Ther. Patents*, 13: 499-510 (2003).

SUMMARY OF THE INVENTION

The present invention is directed to novel fused triazole derivatives which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to fused triazole derivatives that are useful as inhibitors of dipeptidyl peptidase-IV. Compounds of the present invention are described by structural formula I:

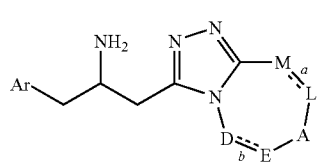

and pharmaceutically acceptable salts thereof; wherein

"a" and "b" represent single or double bonds;

Ar is phenyl, which is unsubstituted or substituted with one to five $R^3$ substituents;

each $R^3$ is independently selected from the group consisting of:
(1) halogen,
(2) $C_{1-6}$ alkyl, which is unsubstituted or substituted with one to five halogens,
(3) $C_{1-6}$ alkoxy, which is unsubstituted or substituted with one to five halogens,
(4) CN, and
(5) hydroxy;

A is $CH_2$, O, S, or a single bond;

D-E together are —$CH_2CH_2$— or —CH=CH—, when A is a single bond; or —$CH_2CH_2$— when A is $CH_2$, O, or S;

L-M together represents a fused ring selected from the group consisting of:

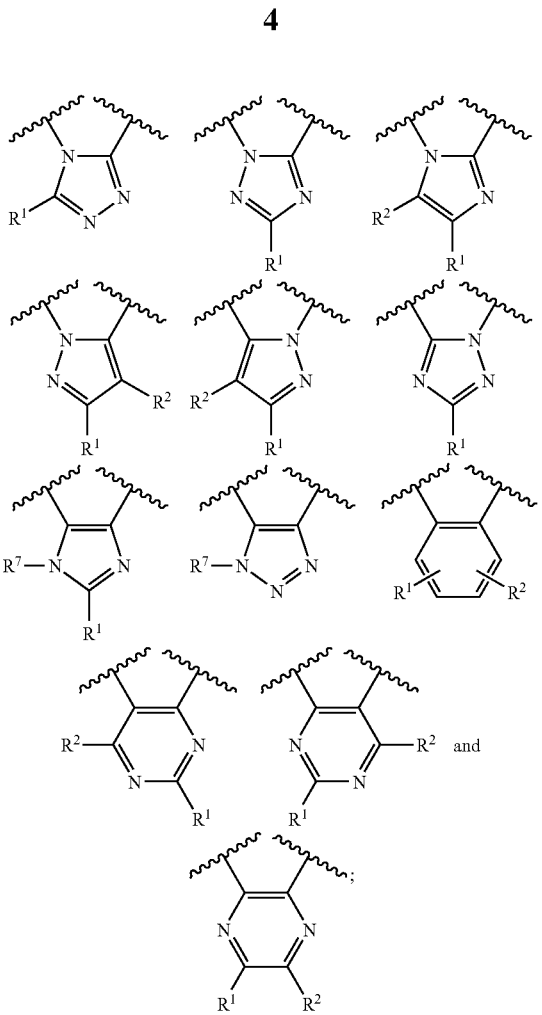

$R^1$ and $R^2$ are each independently selected from the group consisting of:
(1) hydrogen,
(2) $C_{1-10}$ alkyl, which is unsubstituted or substituted with:
 (a) one to five halogens or
 (b) phenyl, which is unsubstituted or substituted with one to five substituents independently selected from halogen, CN, OH, $R^4$, $OR^4$, $NHSO_2R^4$, $N(C_{1-6}$ alkyl)$SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl which is unsubstituted or substituted with one to five substituents independently selected from halogen, CN, OH, $R^4$, $OR^4$, $NHSO_2R^4$, $N(C_{1-6}$ alkyl)$SO_2R^4$, $SO_2R^4$, $SO_2NR^5R^6$, $NR^5R^6$, $CONR^5R^6$, $CO_2H$, and $CO_2C_{1-6}$ alkyl,
(4) a 5- or 6-membered heterocycle which may be saturated or unsaturated containing one to four heteroatoms independently selected from N, S and O, said heterocycle being unsubstituted or substituted with one to three substituents independently selected from oxo, halogen, $NO_2$, CN, OH, $R^4$, $OR^4$, $NHSO_2R^4$, $N(C_{1-6}$ alkyl)$SO_2R^4$, $SO_2R^4$, $SO_2NR^5R^6$, $NR^5R^6$, $CONR^5R^6$, $CO_2H$, and $CO_2C_{1-6}$ alkyl,
(5) $C_{3-6}$ cycloalkyl, which is unsubstituted or substituted with one to three substituents independently selected from halogen, OH, $C_{1-6}$ alkyl, and $C_{1-6}$ alkoxy, wherein alkyl and alkoxy are optionally substituted with one to five halogens,
(6) OH,
(7) $OR^4$,
(8) $SR^4$,
(9) $SO_2R^4$,
(10) $SO_2NR^5R^6$,
(11) $NR^5R^6$,
(12) CN,
(13) $CO_2H$,
(14) $CO_2C_{1-6}$ alkyl,
(15) $CONR^5R^6$, and
(16) halogen;

$R^4$ is $C_{1-6}$ alkyl, which is unsubstituted or substituted with one to five substituents independently selected from halogen, $CO_2H$, and $CO_2C_{1-6}$ alkyl;

$R^5$ and $R^6$ are each independently selected from the group consisting of:
(1) hydrogen,
(2) phenyl, which is unsubstituted or substituted with one to five substituents independently selected from halogen, OH, $C_{1-6}$ alkyl, and $C_{1-6}$ alkoxy, wherein alkyl and alkoxy are optionally substituted with one to five halogens,
(3) $C_{3-6}$ cycloalkyl, which is unsubstituted or substituted with one to three substituents independently selected from halogen, OH, $C_{1-6}$ alkyl, and $C_{1-6}$ alkoxy, wherein alkyl and alkoxy are optionally substituted with one to five halogens, and
(4) $C_{1-6}$ alkyl, which is unsubstituted or substituted with a substituent selected from the group consisting of:
 (a) one to five halogens,
 (b) OH,
 (c) $C_{1-6}$ alkoxy, and
 (d) phenyl, which is unsubstituted or substituted with one to five substituents independently selected from halogen, OH, $C_{1-6}$ alkyl, and $C_{1-6}$ alkoxy, wherein alkyl and alkoxy are optionally substituted with one to five halogens;
or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and $R^7$ is hydrogen or $C_{1-4}$ alkyl.

One embodiment of the present invention encompasses compounds of the formula Ia:

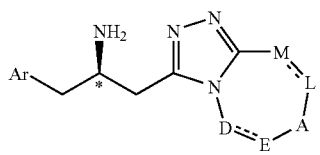

(Ia)

wherein the stereogenic carbon atom atom marked with an * has the R stereochemical configuration and wherein Ar, A, D-E, and L-M are as defined above.

A second embodiment of the present invention encompasses compounds of the formula Ib:

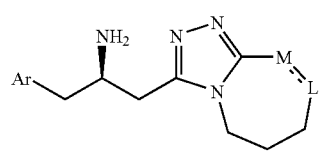

(Ib)

wherein Ar and L-M are as defined above.

One class of this second embodiment encompasses compounds of the formula Ib1:

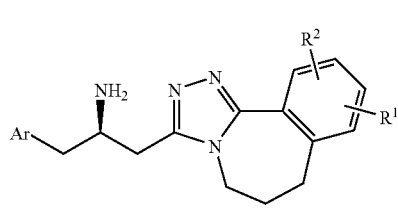

(Ib1)

wherein Ar, $R^1$, and $R^2$ are as defined above.

Another class of this second embodiment encompasses compounds of the formula Ib2:

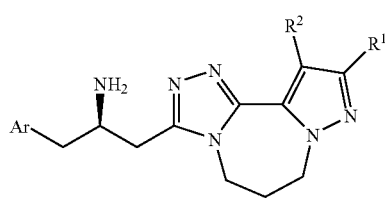

(Ib2)

wherein Ar, $R^1$, and $R^2$ are as defined above.

A third embodiment of the present invention encompasses compounds of the formula Ic:

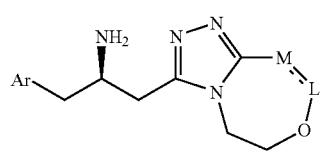

(Ic)

wherein Ar and L-M are as defined above.

One class of this third embodiment encompasses compounds of the formula Ic1:

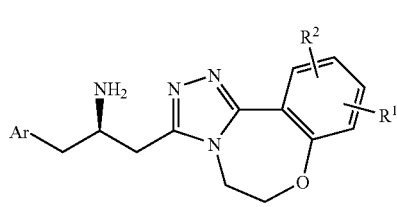
(Ic1)

wherein Ar, $R^1$, and $R^2$ are as defined above.

A fourth embodiment of the present invention encompasses compounds of the formula Id:

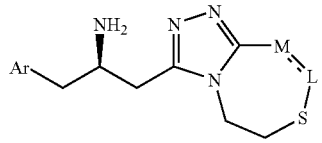
(Id)

wherein Ar and L-M are as defined above.

One class of this fourth embodiment encompasses compounds of the formula Id1:

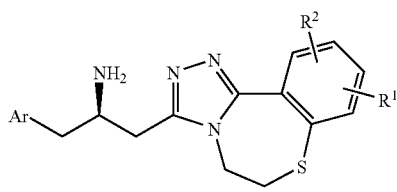
(Id1)

wherein Ar, $R^1$, and $R^2$ are as defined above.

A fifth embodiment of the present invention encompasses compounds of the formula Ie:

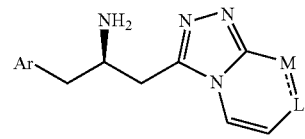
(Ie)

wherein Ar and L-M are as defined above.

One class of this fifth embodiment encompasses compounds of the formula Ie1:

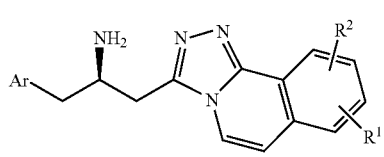
(Ie1)

wherein Ar, $R^1$, and $R^2$ are as defined above.

A second class of this fifth embodiment encompasses compounds of the formula Ie2:

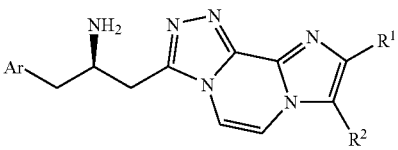
(Ie2)

wherein Ar, $R^1$, and $R^2$ are as defined above.

A third class of this fifth embodiment encompasses compounds of the formula Ie3:

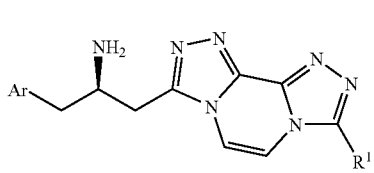
(Ie3)

wherein Ar and $R^1$ are as defined above.

A fourth class of this fifth embodiment encompasses compounds of the formula Ie4:

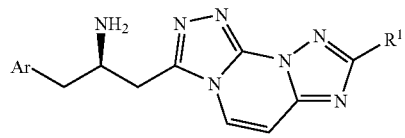
(Ie4)

wherein Ar and $R^1$ are as defined above.

A fifth class of this fifth embodiment encompasses compounds of the formula Ie5:

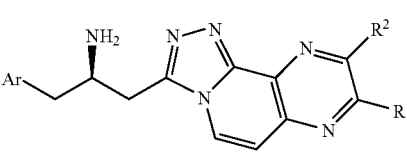
(Ie5)

wherein Ar, $R^1$, and $R^2$ are as defined above.

A sixth class of this fifth embodiment encompasses compounds of the formula Ie6:

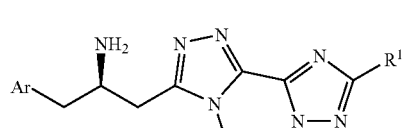
(Ie6)

wherein Ar and $R^1$ are as defined above.

A seventh class of this fifth embodiment encompasses compounds of the formula Ie7:

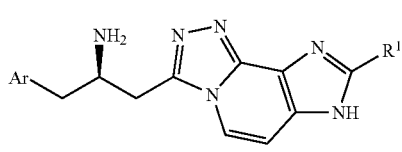

(Ie7)

wherein Ar and $R^1$ are as defined above.

An eighth class of this fifth embodiment encompasses compounds of the formula Ie8:

(Ie8)

wherein Ar is as defined above.

A ninth class of this fifth embodiment encompasses compounds of the formula Ie9:

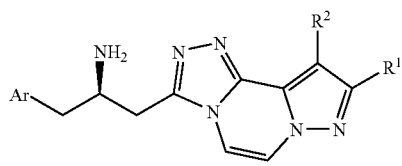

(Ie9)

wherein Ar, $R^1$, and $R^2$ are as defined above.

A sixth embodiment of the present invention encompasses compounds of the formula If:

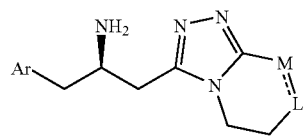

(If)

wherein Ar and L-M are as defined above.

One class of this sixth embodiment encompasses compounds of the formula If1:

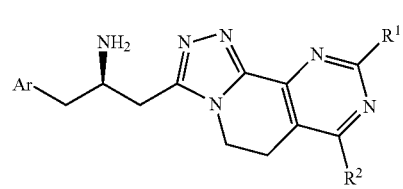

(If1)

wherein Ar, $R^1$, and $R^2$ are as defined above.

A second class of this sixth embodiment encompasses compounds of the formula If2:

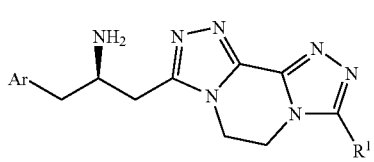

(If2)

wherein Ar and $R^1$ are as defined above.

A third class of this sixth embodiment encompasses compounds of the formula If3:

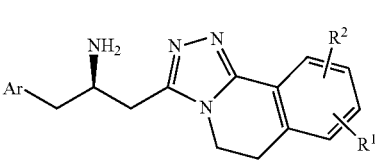

(If3)

wherein Ar, $R^1$, and $R^2$ are as defined above.

A fourth class of this sixth embodiment encompasses compounds of the formula If4:

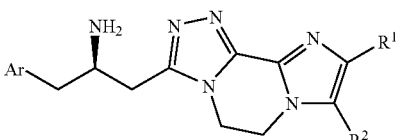

(If4)

wherein Ar, $R^1$, and $R^2$ are as defined above.

A fifth class of this sixth embodiment encompasses compounds of the formula If5:

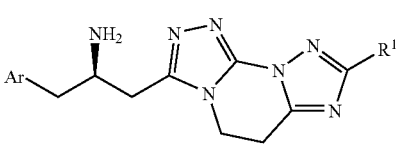

(If5)

wherein Ar and $R^1$ are as defined above.

A sixth class of this sixth embodiment encompasses compounds of the formula If6:

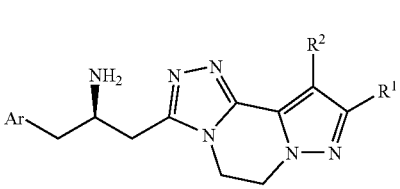

(If6)

wherein Ar, $R^1$, and $R^2$ are as defined above.

A seventh class of this sixth embodiment encompasses compounds of the formula If7:

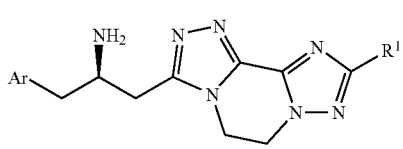

(If7)

wherein Ar and $R^1$ are as defined above

In a seventh embodiment, Ar is phenyl which is unsubstituted or substituted with one to five $R^3$ substituents which are independently selected from the group consisting of:
(1) fluoro,
(2) chloro,
(3) bromo,
(4) methyl,
(5) $CF_3$, and
(6) OH.

In a class of this seventh embodiment, Ar is selected from the group consisting of:
(1) phenyl,
(2) 2-fluorophenyl,
(3) 3,4-difluorophenyl,
(4) 2,5-difluorophenyl, and
(5) 2,4,5-trifluorophenyl.

In an eighth embodiment, A is a single bond or $CH_2$.

In a ninth embodiment, D-E-A together are —$CH_2CH_2$—, —$CH_2CH_2CH_2$—, or —CH=CH—

In a tenth embodiment L-M together represents a fused ring selected from the group consisting of:

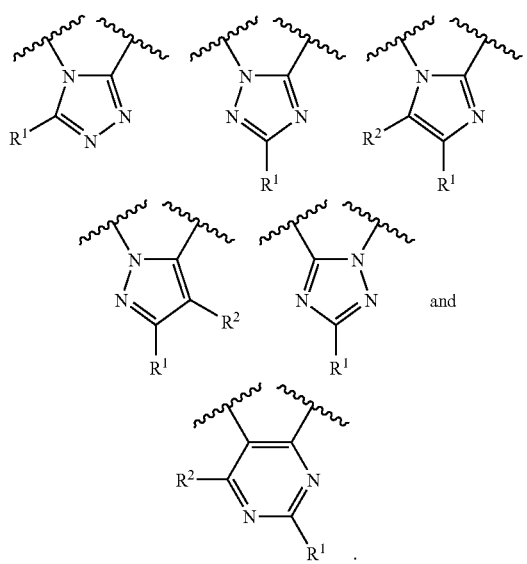

and

In an eleventh embodiment, $R^1$ and $R^2$ are each independently selected from the group consisting of:
(1) hydrogen,
(2) $C_{1-6}$ alkyl, which is unsubstituted or substituted with phenyl or one to five fluorines,
(3) phenyl which is unsubstituted or substituted with one to five substituents independently selected from halogen, $R^4$, $OR^4$, $SR^4$, $SO_2R^4$, $SO_2NR^5R^6$, $NR^5R^6$, $CONR^5R^6$, $CO_2H$, and $CO_2C_{1-6}$alkyl, (4) a 5- or 6-membered heterocycle which may be saturated or unsaturated comprising one to four heteroatoms independently selected from N, S and O, the heterocycle being unsubstituted or substituted with 1-3 substituents independently selected from oxo, halogen, OH, $R^4$, $OR^4$, $SR^4$, $SO_2R^4$, $SO_2NR^5R^6$, $NR^5R^6$, $CONR^5R^6$, $CO_2H$, and $CO_2C_{1-6}$ alkyl,
(5) $C_{3-6}$ cycloalkyl,
(6) $OR^4$,
(7) $SR^4$,
(8) $SO_2R^4$,
(9) $SO_2NR^5R^6$,
(10) $NR^5R^6$,
(11) $CO_2C_{1-6}$ alkyl,
(12) $CONR^5R^6$, and
(13) halogen.

In a class of this eleventh embodiment, $R^1$ and $R^2$ are each independently selected from the group consisting of:
(1) hydrogen,
(2) methyl,
(3) $CF_3$,
(4) phenyl which is unsubstituted or substituted with one to three substituents independently selected from F, Cl, $CH_3$, $CF_3$, OMe, $OCF_3$, SMe, $SO_2Me$, $SO_2NMe_2$, $NMe_2$, and $CONMe_2$,
(5) pyridine, pyrimidine, pyrazine, thiophene, or thiazole which is unsubstituted or substituted with 1 to 2 substituents independently selected from Me, OMe, and $CF_3$,
(6) cyclopropyl,
(7) OMe,
(8) SMe,
(9) $SO_2Me$,
(10) $SO_2NMe_2$,
(11) $NR^5R^6$,
(12) $CO_2C_{1-4}$ alkyl,
(13) $CONR^5R^6$, and
(14) halogen.

In a subclass of this class, $R^1$ and $R^2$ are each independently selected from the group consisting of:
(1) hydrogen,
(2) methyl,
(3) $CF_3$,
(4) phenyl which is unsubstituted or substituted with one to three fluorines,
(5) $CO_2C_{1-4}$ alkyl,
(6) $CONR^5R^6$,
(7) fluorine, and
(8) chlorine.

In a twelfth embodiment, $R^5$ and $R^6$ are each independently selected from the group consisting of:
(1) hydrogen,
(2) phenyl, which is unsubstituted or substituted with one to three substituents independently selected from F, Cl, Me, $CF_3$, OMe, and $OCF_3$,
(3) $C_{3-6}$ cycloalkyl,
(4) $C_{1-6}$ alkyl, which is linear or branched and which is unsubstituted or substituted with:
(a) halogen,
(b) OH,
(c) $C_{1-4}$ alkoxy, and
(d) phenyl, which is unsubstituted or substituted with one to five fluorines;

or wherein R⁵ and R⁶ together with the nitrogen atom to which they are attached form a heterocyclic ring selected from azetidine, pyrrolidine, piperidine, piperazine, and morpholine wherein said heterocyclic ring is unsubstituted or substituted with one or two substituents independently selected from fluoro, hydroxy, Me, and OMe.

In a class of this twelfth embodiment, R⁵ and R⁶ are each independently selected from the group consisting of:
(1) hydrogen,
(2) cyclopropyl, and
(3) $C_{1-4}$ alkyl, which is linear or branched and which is unsubstituted or substituted with fluoro, OH, $C_{1-4}$ alkoxy;

or wherein R⁵ and R⁶ together with the nitrogen atom to which they are attached form a heterocyclic ring selected from azetidine, pyrrolidine, piperidine, piperazine, and morpholine wherein said heterocyclic ring is unsubstituted or substituted with one or two substituents independently selected from fluoro, hydroxy, Me, and OMe.

Illustrative, but nonlimiting, examples of compounds of the present invention that are useful as DPP-IV inhibitors are the following:

(2R)-1-[9-(trifluoromethyl)-5,6-dihydro[1,2,4]triazolo[4',3':1,2]pyrido[3,4-d]pyrimidin-3-yl]-3-(2,4,5-trifluorophenyl)propan-2-amine

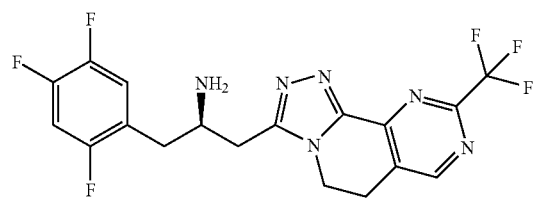

(2R)-1-[8-(trifluoromethyl)-5,6-dihydrobis[1,2,4]triazolo[3,4-c:4',3'-a]pyrazin-3-yl]-3-(2,4,5-trifluorophenyl)propan-2-amine

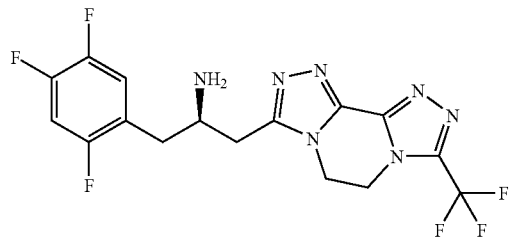

(2R)-1-[9-(trifluoromethyl)-5,6-dihydrobis[1,2,4]triazolo[1,5-a:3',4'-c]pyrazin-3-yl]-3-(2,4,5-trifluorophenyl)propan-2-amine

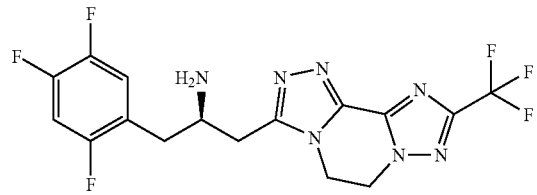

(2R)-1-[9-(trifluoromethyl)-5,6-dihydroimidazo[1,2-a][1,2,4]triazolo[3,4-c]pyrazin-3-yl]-3-(2,4,5-trifluorophenyl)propan-2-amine

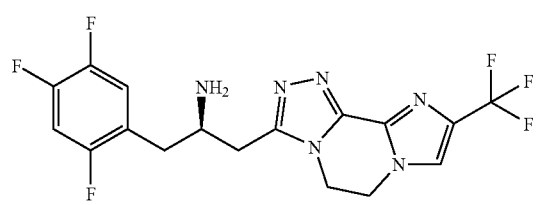

methyl-3-[(2R) -2-amino-3-(2,5-difluorophenyl)propyl]-6,7-dihydro-5H-pyrazolo[1,5-a][1,2,4]triazolo[3,4-c][1,4]diazepine-10-carboxylate

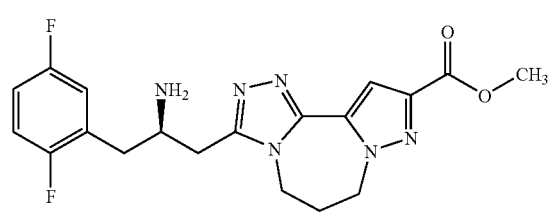

(2R)-1-[9-trifluoromethyl)bis[1,2,4]triazolo[1,5-a:3',4'-c]pyrazin-3yl]-3-(2,4,5-trifluorophenyl)propan-2-amine

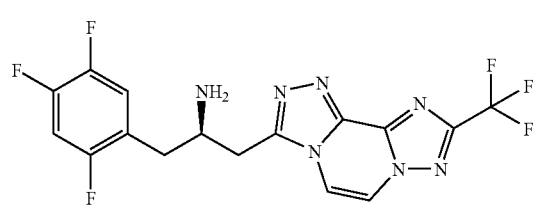

(2R)-1-[10-(pyrrolidin-1-ylcarbonyl)-6,7-dihydro-
5H-pyrazolo[1,5-a][1,2,4]triazolo[3,4-c][1,4]diaz-
epin-3-yl]-3-(2,4,5-trifluorophenyl)propan-2-amine

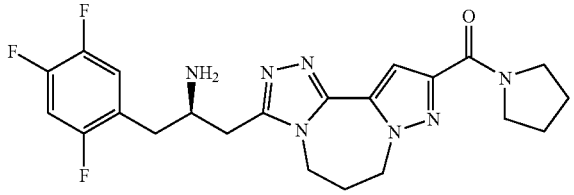

(2R)-1-(8-methyl-5,6-dihydrobis[1,2,4]triazolo[1,5-
c:4',3'-a]pyrimidin-3-yl)-3-(2,4,5-trifluorophenyl)
propan-2-amine

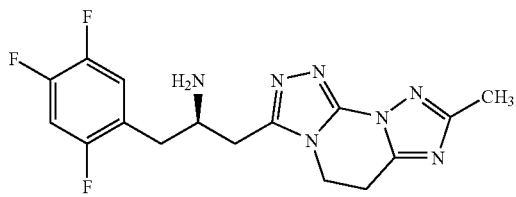

(2R)-1-[8-(trifluoromethyl)bis[1,2,4]triazolo[3,4-c:
4',3'-a]pyrazin-3-yl]-3-(2,4,5-trifluorophenyl)propan-
2-amine

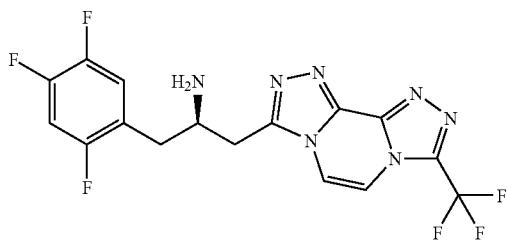

(2R)-1-[10-(trifluoromethyl)-6,7-dihydro-5H-pyra-
zolo[1,5-a][1,2,4]triazolo[3,4-c][1,4]diazepin-3yl]-3-
(2,4,5-trifluorophenyl)propan-2-amine

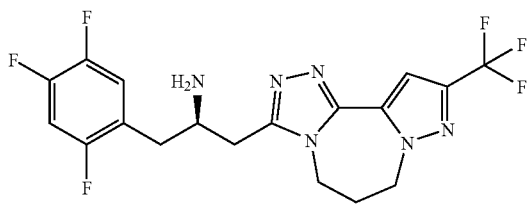

(2R)-1-[9-(trifluoromethyl)-5,6-dihydropyrazolo[1,
5-a][1,2,4]triazolo[3,4-c]pyrazin-3-yl]-3-(2,4,5-trif-
luorophenyl)propan-2-amine

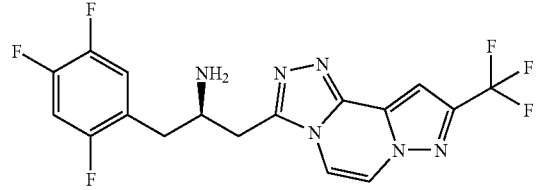

(2R)-1-[8-(trifluoromethyl)-5,6-dihydrobis[1,2,4]
triazolo[1,5-c:4',3'-a]pyrimidin-3-yl]-3-(2,4,5-trifluo-
rophenyl)propan-2-amine

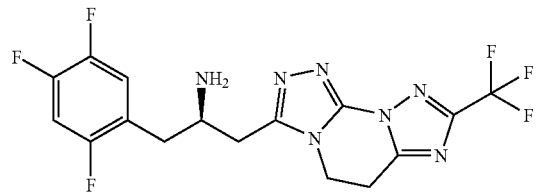

and the pharmaceutically acceptable salts thereof.

Further illustrative of the compounds of the present invention that are useful as DPP-IV inhibitors are the following:

(2R)-1-[8-(trifluoromethyl)-5,6-dihydrobis[1,2,4]
triazolo[1,5-c:4',3'-a]pyrimidin-3-yl]-3-(2,4,5-trifluo-
rophenyl)propan-2-amine (2R)-1-[9-(trifluoromethyl)-5,6-dihydrobis[1,2,4]
triazolo[1,5-a:3',4'-c]pyrazin-3-yl]-3-(2,4,5-trifluo-
rophenyl)propan-2-amine

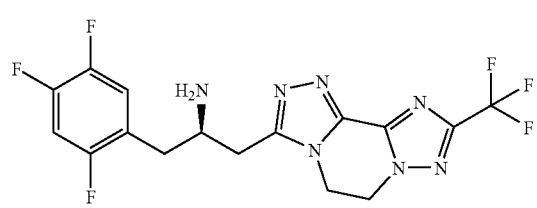

and the pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-10}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. In particular the compounds of the present invention have an asymmetric center at the stereogenic carbon atoms marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia show the preferred stereochemistry at the stereogenic carbon atom to which is attached the $NH_2$ group.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue.

The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m=50\,\mu M$; $k_{cat}=75\,s^{-1}$; $k_{cat}/K_m=1.5\times10^6\,M^{-1}s^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by nonlinear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (eg. PACAP). Inactivation of these peptides by DPP-IV may also play a role in glucose homeostasis. The DPP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine.* 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine* 6: 802-807 (2000)). In addition, studies with DPP-IV deficient mice suggest that these animals are resistant to diet-induced obesity and associated pathology (e.g. hyperinsulinonemia).

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DPP-IV inhibitor diprotin A; and (3) GRF [3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-IV, may exhibit trophic effects on the intestinal epithelium (*Regulatory Peptides* 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation*, 63: 1495-1500 (1997)). DPP-IV inhibitors have been tested in collagen and alkyldiamine-induced arthritis in rats and showed a statistically significant attenuation of hind paw swelling in this model [Int. J. Immunopharmacology 19:15-24 (1997) and Immunopharmacology, 40: 21-26 (1998)]. DPP-IV is upregulated in a number of autoimmune diseases including rheumatoid arthritis, multiple sclerosis, Graves' disease, and Hashimoto's thyroiditis (*Immunology Today*. 20: 367-375 (1999)).

HIV Infection: DPP-IV inhibition may be useful for the treatment or prevention of HIV infection or AIDS because a number of chemokines which inhibit HIV cell entry are potential substrates for DPP-IV (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DPP-IV would be expected to decrease HIV infectivity.

Hematopoiesis: DPP-IV inhibition may be useful for the treatment or prevention of hematopiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6 M^{-1}s^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-IV have an anxiolytic phenotype (WO 02/34243; Karl et al., *Physiol. Behav.* 2003). DPP-IV deficient mice also have an anxiolytic phenotype using the porsolt and light/dark models. Thus DPP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-IV inhibitors are expected to show similar effects Myocardial Infarction: GLP-1 has been shown to be beneficial when administered to patients following acute myocardial infarction (Circulation, 109: 962-965 (2004)). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.*, 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (*Eur. J. Clin. Chem. Clin. Biochem.*, 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.*, 37: 167-173 (1992)).

Osteoporosis: DPP-IV inhibition may be useful for the treatment or prevention of osteoporosis because GIP receptors are present in osteoblasts.

Stem Cell Transplantation: Inhibition of DPP-IV on donor stem cells has been shown to lead to an enhancement of their bone marrow homing efficiency and engraftment, and an increase in survival in mice (Christopherson, et al., Science, 305:1000-1003 (2004)). Thus DPP-IV inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an-amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HmG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), cholecystokinin 1 (CCK-1) receptor agonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Part. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24

Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidide (P32/98); NVP-DPP-728; vildagliptin (LAF 237); P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of antiobesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 January 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6699873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02//092566, WO 03/-093234, WO 03/095474, and WO 03/104761.

The potential utility of safe and effective activators of glucokinase (GKAs) for the treatment of diabetes is discussed in J. Grimsby et al., "Allosteric Activators of Glucokinase: Potential Role in Diabetes Therapy," *Science*, 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1: 1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day.

Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared, by various routes, from beta amino acid intermediates such as those of formula II and substituted heterocyclic intermediates such as those of the general formula III,

II

III wherein Ar, A, D-E, and L-M are as defined above; P is a suitable nitrogen protecting group such as tert-butoxycarbonyl, benzyloxycarbonyl, or 9-fluorenylmethoxycarbonyl; and X is NHNH$_2$ or a suitable leaving group such as Cl, OMe, SMe, or =S. The preparation of these intermediates and their conversion to compounds of formula I are described in the following Schemes.

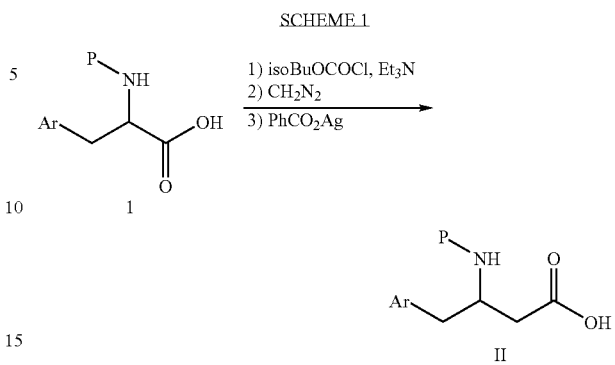

Compounds of formula II are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, di-tert-butyl-dicarbonate (for P=Boc), carbobenzyloxy chloride (for P=Cbz), or N-(9-fluorenylmethoxycarbonyloxy) succinimide (for P=Fmoc), is treated with isobutyl chloroformate and a base such as triethylamine or N,N-diisopropylethylamine, followed by diazomethane. The resultant diazoketone is then treated with silver benzoate in a solvent such as methanol or aqueous dioxane and may be subjected to sonication following the procedure of Sewald et al., *Synthesis*, 837 (1997) in order to provide the beta amino acid II. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Enantioselective Synthesis of β-Amino Acids*, Ed., Wiley-VCH, New York: 1997, Juaristi et al., *Aldrichimica Acta*, 27, 3 (1994), Cole et al., *Tetrahedron*, 32, 9517 (1994).

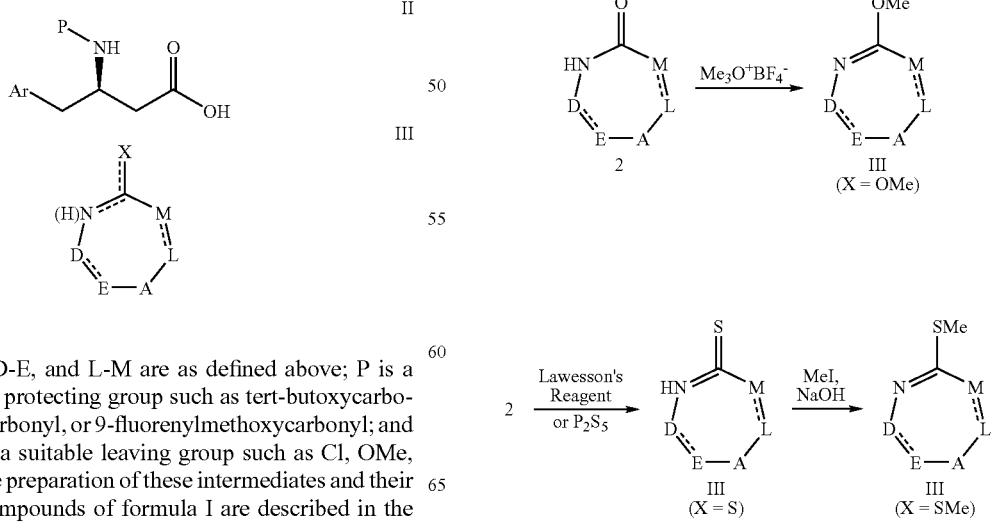

-continued

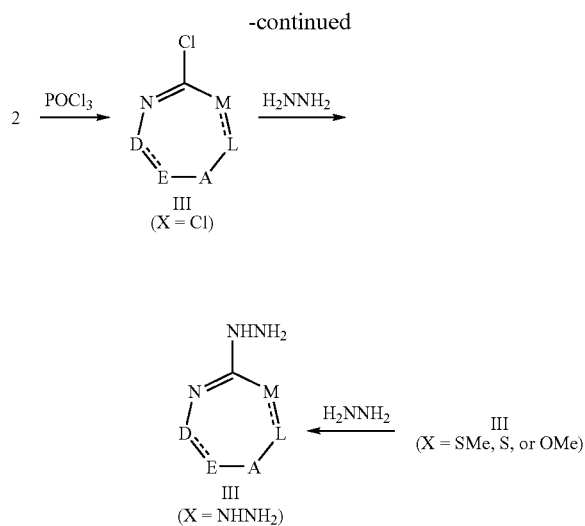

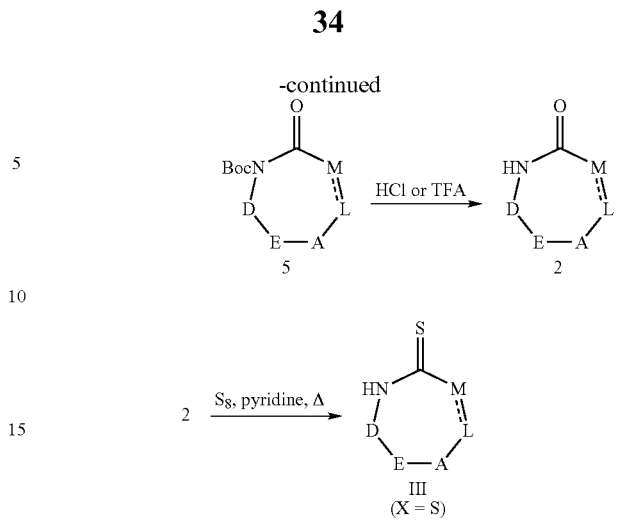

Intermediates 2, from Scheme 2, are themselves commercially available, known in the literature or may be conveniently prepared by a variety of methods familiar to those skilled in the art. One such method when D-E is CH$_2$CH$_2$ is illustrated in Scheme 3. Cyclic secondary amine 3 is first Boc-protected by reaction with di-tert-butyl dicarbonate in the presence of a base such as N,N-diisopropylethylamine or triethylamine in a solvent such as dichloromethane to give 4. The activated methylene group is then selectively oxidized to carbonyl by catalytic ruthenium dioxide in the presence of sodium periodate in ethyl acetate-water according to the method of S. Yoshifuji and M. Kaname, *Chem. Pharm. Bull.,* 43, 1302 (1995), yielding 5. The Boc group is readily removed with anhydrous hydrogen chloride in a solvent such as dioxane, or alternatively with trifluoroacetic acid (neat or diluted with a solvent such as dichloromethane), to give 2, which can be processed further as in Scheme 2. Also, as shown in Scheme 3, reaction of certain 3 with sulfur in pyridine at reflux temperature, as described by K. I. Ajzert and K. Takács, *Liebigs Ann. Chem.,* 1061 (1987), affords thiolactam III (X=S), which can be carried forward as in Scheme 2. In addition to the general methods illustrated in Schemes 2 and 3, compounds of formula III may be prepared by various routes known in the literature, and specific examples are described in the experimental section that follows.

Compounds of formula III are commercially available, known in the literature, or may be conveniently prepared by a variety of methods familiar to those skilled in the art. Some convenient methods are shown in Scheme 2. Lactam derivative 2 is O-methylated, for example, by treatment with trimethyloxonium tetrafluoroborate in the presence of sodium carbonate in a solvent such as dichloromethane to provide compound EEL (X=OMe). Treatment of 2 with Lawesson's Reagent in a solvent such as xylenes or toluene at reflux temperature provides compound In (X=S). Alternatively, this intermediate may be obtained by treatment of 2 with phosphorus pentasulfide in a solvent such as pyridine at reflux temperature or by treatment of 2 with the phosphorus pentasulfide-sodium carbonate complex [see, for example, D. Brillon, *Synth. Commun.,* 20, 3085 (1990] in a solvent such as tetrahydrofuran at about 20-60° C. Compound III (X=S) may be methylated by standard methods [for example, by treatment of a solution or suspension of III (X=S) in 50% sodium hydroxide with iodomethane, as reported by O. Cherkaoui et al., *Tetrahedron Lett.,* 31, 5467 (1990)] to give III (X=SMe). Especially where D-E is CH=CH and A is a single bond, compound III (X=Cl) may be obtained by treatment of 2 with a deoxychlorinating agent such as phosphorus oxychloride or phenylphosphonic dichloride at a temperature of about 100-150° C. It is sometimes advantageous to conduct this reaction in the presence of an activating agent such as N,N-diethylaniline. Further treatment of compound In (X=Cl) with an excess of hydrazine affords compound III (X=NHNH$_2$). In certain cases, a compound of formula III (X=NHNH$_2$) may also be obtained by treatment of III (X=SMe, S, or OMe) with an excess of hydrazine, typically in a solvent such as ethanol, at reflux temperature.

SCHEME 3

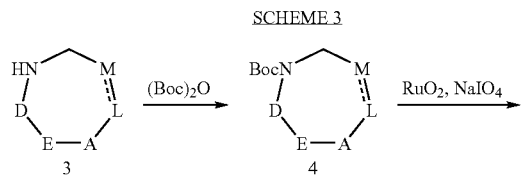

SCHEME 4

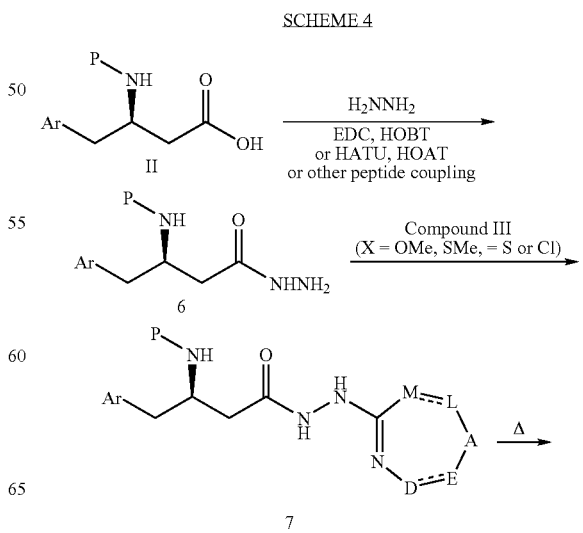

-continued

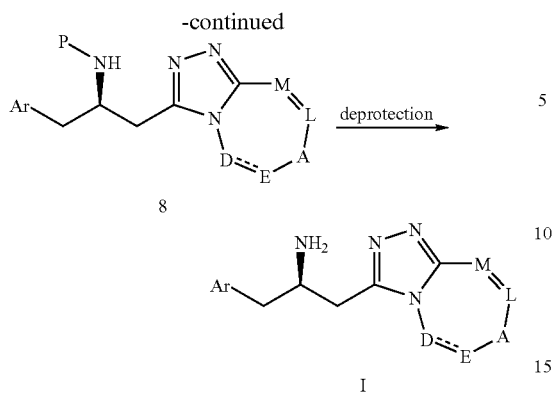

SCHEME 5

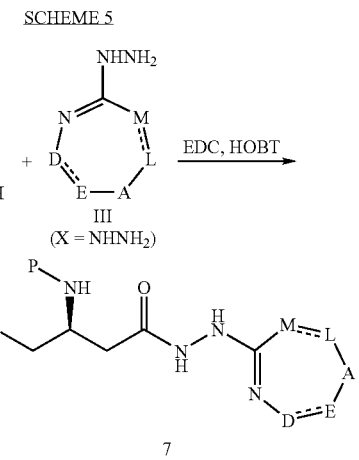

As shown in Scheme 4, an N-protected beta amino acid of formula II can be converted to its acyl hydrazide derivative 6 by treatment with an excess of hydrazine in the presence of standard peptide coupling reagents such as 1-(3-dimethylaminopropyl)-3-ethylcarbodiimide hydrochloride (EDC) and 1-hydroxybenzotriazole (HOBT) or O-(7-azabenzotriazol-1-yl)-N,N,N',N'-tetramethyluronium hexafluorophosphate (HATU) and 1-hydroxy-7-azabenzotriazole (HOAT) in the presence of a tertiary amine base such as N,N-diisopropylethylamine or triethylamine, in a solvent such as dichloromethane or N,N-dimethylformamide (DMF). Similarly, using the acyl hydrazide synthesis method of U. Boas et al., Syn. Conmm., 28, 1223 (1998), the reaction can be conducted with the coupling agent 2-fluoro-1,3-dimethylimidazolidinium hexafluorophosphate in the presence of a tertiary amine such as triethylamine, in a solvent such as DMF. Reaction of 6 with a compound of formula III (X═OMe, SMe, ═S, or Cl) in a solvent such as 2-methoxyethanol, n-butanol, methanol, or acetic acid, at a temperature of about 20-130° C., affords the adduct 7, which may be cyclized to the fused triazole derivative 8 by further heating at about 100-150° C. in a solvent such as 2-methoxyethanol or xylenes. The intermediate 7 is not always isolated, and it is sometimes convenient to prepare 8 directly from 6 by heating with III in a solvent such as 2-methoxyethanol or xylenes at the boiling point. Analogous formation of fused triazole derivatives by one-step or two-step methods has been reported by several investigators, for example: S. Petersen et al., U.S. Pat. No. 2,913, 454 (1959); D. R. Shridhar et al. Indian J. Chem., 20B, 132 (1981); M. Langlois et al., J. Heterocycl. Chem., 19, 193 (1982); M. Bonanomi and L. Baiocchi, J. Heterocycl. Chem., 20, 1657 (1983); O. Cherkaoui et al., Tetrahedron Lett., 31, 5467 (1990); and G. A. McCort and J. C. Pascal, Tetrahedron Lett, 33, 4443 (1992). Deprotection of 8 is accomplished by standard methods to provide a compound of formula I. For example, where the protecting group is tert-butoxycarbonyl (Boc), deprotection may be accomplished conveniently by treatment of 8 with anhydrous HCl, in a solvent such as dioxane or methanol, or with trifluoroacetic acid in dichloromethane. It should be noted that the use of acetic acid at reflux to perform the ring closure of 7 to 8 typically results in replacement of the N—Boc protecting group by N-acetyl. Removal of the N-acetyl group may be accomplished by heating 8 in aqueous 6N HCl at reflux temperature. Where the protecting group is Boc and X═Cl, ring closure and deprotection may proceed, in effect, simultaneously. Even in the case of other X groups (for example, OMe), at least partial concomitant loss of the Boc group may sometimes occur during the ring closure step.

An alternative route for the preparation of intermediate 7 is illustrated in Scheme 5. Reaction of the beta amino acid of formula II with a hydrazino heterocycle of formula III (X═NHNH$_2$) under standard peptide coupling conditions (for example, EDC and HOBT in the presence of a tertiary amine such as N,N-diisopropylethylamine, in a solvent such as DMF or dichloromethane) provides 7, which may be carried forward as shown in Scheme 4. Related conversions of acid derivatives and hydrazino heterocycles to acylhydrazino heterocycles and then to fused triazoles have been described in the literature [see, for example, H. K. Reimlinger and J. J. M. Vandewalle, U. S. Pat. No. 3,775,416 (1973)].

SCHEME 6

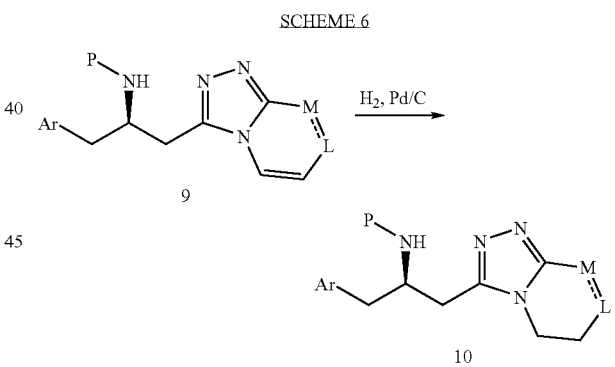

In the case of protected derivative 9, corresponding to 8 in which A is a single bond and D-E together are CH═CH, it is sometimes convenient to prepare the dihydro derivative 10 by catalytic hydrogenation, as illustrated in Scheme 6. Thus, 10 may be obtained by shaking or stirring a mixture of 9, palladium on carbon catalyst, and a solvent such as 2-methoxyethanol with hydrogen, at a pressure of about 1-4 atm. Deprotection of 10 as described in Scheme 4 provides a compound of formula I wherein A is a single bond and D-E together are CH$_2$CH$_2$.

Following deprotection, the amine of formula I is purified from unwanted side products, if necessary, by recrystallization, trituration, preparative thin layer chromatography, flash chromatography on silica gel as described by W. C. Still et al, J. Org. Chem., 43, 2923 (1978), or HPLC. Compounds which are purified by HPLC may be isolated as the corresponding salt. Purification of intermediates is achieved in the same manner.

In some cases the intermediate 8, obtained as described in Scheme 4, may be further modified before removal of the protecting group, for example, by manipulation of $R^1$ and/or $R^2$ substituents on the fused ring indicated by L-M. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

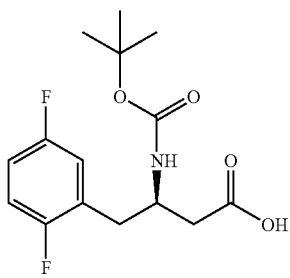

(3R)-3-[(tert-Butoxycarbonyl)amino]-4-(2,5-difluorophenyl)butanoic acid

Step A: (R,S)-N-(tert-Butoxycarbonyl)-2,5-difluorophenylalanine

To a solution of 0.5 g (2.49 mmol) of 2,5-difluoro-DL-phenylalanine in 5 mL of tert-butanol were added sequentially 1.5 mL of 2N aqueous sodium hydroxide solution and 543 mg of di-tert-butyl dicarbonate. The reaction was stirred at ambient temperature for 16 h and diluted with ethyl acetate. The organic phase was washed sequentially with 1N hydrochloric acid and brine, dried over magnesium sulfate and concentrated in vacuo. The crude material was purified by flash chromatography (silica gel, 97:2:1 dichloromethane:methanol:acetic acid) to afford the title compound. LC/MS 302 (M+1).

Step B: (R,S)-3-[(tert-Butoxycarbonyl)amino]-1-diazo-4-(2,5-difluoro-phenyl)butan-2-one To a solution of 2.23 g (7.4 mmol) of (R,S)-N-(tert-butoxycarbonyl)-2,5-difluorophenylalanine in 100 mL of diethyl ether at 0° C. were added sequentially 1.37 mL (8.1 mmol) of triethylamine and 0.931 mL (7.5 mmol) of isobutyl chloroformate and the reaction was stirred at this temperature for 15 min. A cooled ethereal solution of diazomethane was then added until the yellow color persisted and stirring was continued for a further 16 h. The excess diazomethane was quenched by dropwise addition of acetic acid, and the reaction was diluted with ethyl acetate and washed sequentially with 5% hydrochloric acid, saturated aqueous sodium bicarbonate solution and brine, dried over magnesium sulfate and concentrated in vacuo. Purification by flash chromatography (silica gel, 4:1 hexane:ethyl acetate) afforded the diazoketone.

$^1$H NMR (500 MHz, CDCl$_3$): δ 7.03-6.95 (m, 1H), 6.95-6.88 (m, 2H), 5.43 (bs, 1H), 4.45 (bs, 1H), 3.19-3.12 (m, 1H), 2.97-2.80 (m, 1H), 1.38 (s, 9H).

Step C: (3R)-3-[(tert-Butoxycarbonyl)amino]-4-(2,5-difluorophenyl)butanoic acid

To a solution of 2.14 g (6.58 mmol) of (R,S)-3-[(tert-butoxycarbonyl)-amino]-1-diazo-4-(2,5-difluorophenyl)butan-2-one dissolved in 100 mL of methanol at −30° C. were added sequentially 3.3 mL (19 mmol) of N,N-diisopropylethylamine and 302 mg (1.32 mmol) of silver benzoate. The reaction was stirred for 90 min before diluting with ethyl acetate and washing sequentially with 2N hydrochloric acid, saturated aqueous sodium bicarbonate, and brine. The organic phase was dried over magnesium sulfate, concentrated in vacuo and the enantiomers were separated by preparative chiral HPLC (Chiralpak AD column, 5% ethanol in hexanes) to give 550 mg of the desired (R)-enantiomer, which eluted first. This material was dissolved in 50 mL of a mixture of tetrahydrofuran:methanol: 1N aqueous lithium hydroxide (3:1:1) and stirred at 50° C. for 4 h. The reaction was cooled, acidified with 5% dilute hydrochloric acid and extracted with ethyl acetate. The combined organic phases were washed with brine, dried over magnesium sulfate and concentrated in vacuo to give the title compound as a white foamy solid.

$^1$H NMR (500 MHz, CDCl$_3$): δ 7.21 (m, 1H), 6.98 (m, 2H), 6.10 (bs, 1H), 5.05 (m, 1H), 4.21 (m,1H), 2.98 (m, 2H), 2.60 (m, 2H), 1.38 (s, 9H).

INTERMEDIATE 2

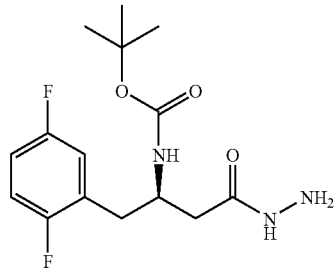

tert-Butyl[(1R)-1-(2,5-difluorobenzyl)-3-hydrazino-3-oxopropyl]carbamate

To a solution of 94.6 mg (0.3 mmol) of (3R)-3-[(tert-butoxycarbonyl)amino]-4-(2,5-difluorophenyl)butanoic acid (Intermediate 1) in 1.5 mL of anhydrous dichloromethane, stirred in an ice bath under protection from moisture, was added 0.0106 mL (10.8 mmol) of anhydrous 98% hydrazine. Then 91.8 mg of 1-hydroxybenzotriazole hydrate was added, followed by 63.4 mg (0.33 mmol) of 1-(3-dimethylaminopropyl)-3-ethylcarbodiimide hydrochloride (EDC) and finally 0.0574 mL (42.6 mg, 0.33 mmol) of N,N-diisopropylethylamine. After 15 minutes, an additional 0.0574 mL (42.6 mg, 0.33 mmol) of N,N-diisopropylethylamine was added. After 2 h, the mixture was removed from the ice bath and allowed to warm to room temperature, and precipitation gradually increased. After 22 h, the precipitated solid was collected on a filter, washed with small volumes of dichloromethane, and dried to give the title compound as a white solid, mp 168-169° C. LC-MS 230 (M+1-Boc).

INTERMEDIATE 3

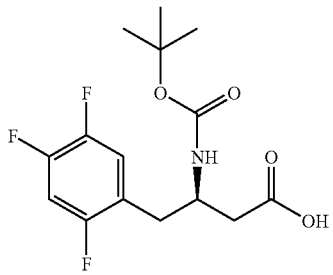

(3R)-3-[(tert-Butoxycarbonyl)amino]-4-(2,4,5-trifluorophenyl)butanoic acid

Step A: (2S,5R)-2,5-Dihydro-3,6-dimethoxy-2-isopropyl-5-(2,4,5-trifluorobenzyl)pyrazine To a solution of 3.42 g (18.5 mmol) of commercially available (2S)-2,5-dihydro-3,6-dimethoxy-2-isopropylpyrazine in 100 mL of tetrahydrofuran at −70° C. was added 12 mL (19 mmol) of a 1.6M solution of butyllithium in hexanes. After stirring at this temperature for 20 min, 5 g (22.3 mmol) of 2,4,5-trifluorobenzyl bromide in 20 mL of tetrahydrofuran was added and stirring was continued for 3 h before warming the reaction to ambient temperature. The reaction was quenched with water, concentrated in vacuo, and extracted with ethyl acetate. The combined organic phase was washed with brine, dried, and concentrated in vacuo. Purification by flash chromatography (silica gel, 0-5% ethyl acetate in hexanes) afforded the title compound.

$^1$H NMR (500 MHz, CDCl$_3$): δ 7.01 (m, 1H), 6.85 (m, 1H), 4.22 (m, 1H), 3.78 (m, 3H), 3.64 (m, 3H), 3.61 (m, 1H), 3.20 (m, 1H), 2.98 (m, 1H), 2.20 (m, 1H), 0.99 (d, 3H, J=8 Hz).

Step B: (R)-N-(tert-Butoxycarbonyl)-2,4,5-trifluorophenylalanine methyl ester To a solution of 3.81 g (11.6 mmol) of (2S,5R)-2,5-dihydro-3,6-dimethoxy-2-isopropyl-5-(2,4,5-trifluorobenzyl)pyrazine in 20 mL of acetonitrile was added 20 mL of 2N hydrochloric acid. The reaction was stirred for 72 h and concentrated in vacuo. The residue was dissolved in 30 mL of dichloromethane and 10 mL (72 mmol) of triethylamine and 9.68 g (44.8 mmol) of di-tert-butyl dicarbonate were added. The reaction was stirred for 16 h, diluted with ethyl acetate and washed sequentially with 1N hydrochloric acid and brine. The organic phase was dried over sodium sulfate, concentrated in vacuo and purified by flash chromatography (silica gel, 9:1 hexanes:ethyl acetate) to afford the title compound.

$^1$H NMR (500 MHz, CDCl$_3$): δ 6.99 (m, 1H), 6.94 (m, 1H), 5.08 (m, 1H), 4.58 (m, 1H), 3.78 (m, 3H), 3.19 (m, 1H), 3.01 (m, 1H), 1.41 (s, 9H).

Step C: (R)-N-(tert-Butoxycarbonyl)-2,4,5-trifluorophenylalanine

A solution of 2.41 g (7.5 mmol) of (R)-N-(tert-butoxycarbonyl)-2,4,5-trifluorophenylalanine methyl ester in approximately 200 mL of a mixture of tetrahydrofuran:methanol: 1N lithium hydroxide (3:1:1) was stirred at 50° C. for 4 h. The reaction was cooled, acidified with 5% hydrochloric acid (aqueous) and extracted with ethyl acetate. The combined organic phases were washed with brine, dried over magnesium sulfate and concentrated in vacuo to give the title compound. LC-MS 220.9 (M+1-BOC).

Step D: (3R)-3-[(tert-Butoxycarbonyl)amino]-4-(2,4,5-trifluorophenyl)-butanoic acid To a solution of 0.37 g (1.16 mmol) of (R)-N-(tert-butoxycarbonyl)-2,4,5-trifluorophenylalanine in 10 mL of diethyl ether at −20° C. were added sequentially 0.193 mL (1.3 mmol) of triethylamine and 0.18 mL (1.3 mmol) of isobutyl chloroformate, and the reaction was stirred at this temperature for 15 min. A cooled ethereal solution of diazomethane was then added until the yellow color persisted and stirring was continued for a further 1 h. The excess diazomethane was quenched by dropwise addition of acetic acid, and the reaction was diluted with ethyl acetate and washed sequentially with saturated aqueous sodium bicarbonate solution and brine, dried over magnesium sulfate and concentrated in vacuo. Purification by flash chromatography (silica gel, 3:1 hexane:ethyl acetate) afforded 0.36 g of diazoketone. To a solution of 0.35 g (1.15 mmol) of the diazoketone dissolved in 12 mL of 1,4-dioxane: water (5:1) was added 26 mg (0.113 mmol) of silver benzoate. The resultant solution was sonicated for 2 h before diluting with ethyl acetate and washing sequentially with 1N hydrochloric acid and brine, drying over magnesium sulfate and concentrating in vacuo. Purification by flash chromatography (silica gel, 97:2:1 dichloromethane:methanol:acetic acid) afforded the title compound.

$^1$H NMR (500 MHz, CDCl$_3$); δ 7.06 (m, 1H), 6.95 (m, 1H), 5.06 (bs, 1H), 4.18 (m, 1H), 2.98 (m, 2H), 2.61 (m, 2H), 1.39 (s, 9H).

INTERMEDIATE 4

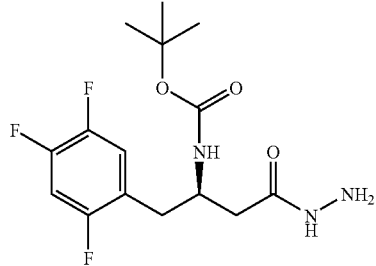

tert-Butyl[(1R)-3-hydrazino-3-oxo-1-(2,4,5-trifluorobenzyl)propyl]carbamate

A dried flask was charged with 1.00 g (3 mmol) of (3R)-3-[(tert-butoxycarbonyl)amino]-4-(2,4,5-trifluorophenyl) butanoic acid (Intermediate 3) and 865 mg (3.3 mmol) of 2-fluoro-1,3-dimethylimidazolidinium hexafluorophosphate, followed by 7.5 mL of anhydrous DMF. The resulting solution was stirred under nitrogen gas with cooling in an ice bath as 0.835 mL of triethylamine was added by syringe through a septum, and this was followed by 0.291 mL (300 mg, 6 mmol) of hydrazine hydrate. After several min, the ice bath was removed, and the mixture was allowed to warm to room temperature. After 1 h, 40 mL of water was added very gradually by syringe, accompanied by vigorous stirring. This resulted in precipitation of product. One hour later, the solid was collected on a filter, washed generously with water, and dried. The crude product was dissolved in dichloromethane-methanol and evaporated onto several grams of silica gel, which was loaded onto the top of a silica gel column. Flash chromatography (1-4% methanol in dichloromethane) provided the title compound as a white solid, mp 168-168.5° C. LC-MS 248 (M+1-Boc).

INTERMEDIATE 5

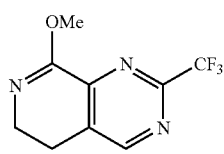

8-Methoxy-2-(trifluoromethyl)-5,6-dihydropyrido[3,4-d]pyrimidine

Step A: 7-Benzyl-2-(trifluoromethyl)-5,6,7,8-tetrahydropyrido[3,4-d]pyrimidin-4-ol To a solution of sodium ethoxide, prepared from 3.2 g (133 mmol) of sodium metal and 200 mL of absolute ethanol, at ambient temperature was added 8.3 g (74 mmol) of trifluoroacetamidine followed by 17.8 g (60 mmol) of ethyl 1-benzyl-3-oxopiperidine-4-carboxylate hydrochloride in portions over 15 min. The reaction mixture was stirred at ambient temperature for 1 h, then heated at reflux for 30 h. The mixture was concentrated in vacuo. The resultant red foam was partitioned between 300 mL of 1N aqueous sodium hydroxide solution and 300 mL of ether. The aqueous layer was washed with 300 mL of diethyl ether and the combined ether phases were extracted with 50 mL of 1N aqueous sodium hydroxide solution. The combined aqueous phases were cooled in an ice-water bath and neutralized to pH 7 with concentration hydrochloric acid. The solids were collected, washed with water, and dried in vacuo to give the title compound as a beige solid, which was used as is in Step B below. An analytical sample was prepared by recrystallization from isopropanol to give the title compound as a white powder.
LC-MS 310 (M+1).

Step B: 7-Benzyl-4-chloro-2-(trifluoromethyl)-5,6,7,8-tetrahydropyrido[3,4-d]pyrimidine A mixture of 29.6 g (95.7 mmol) of 7-benzyl-2-(trifluoromethyl)-5,6,7,8-tetrahydropyrido[3,4-d]pyrimidin-4-ol (prepared essentially as described in Step A, above) and 53 mL of phenylphosphonic dichloride in a 250-mL round bottom flask was heated at 150° C. After 2 h, the reaction was judged to be complete by TLC analysis. The mixture was cooled to ambient temperature and poured onto 400 g of ice, transferring with about 500 mL of ethyl acetate. The aqueous layer was neutralized with solid sodium bicarbonate and the layers separated. The aqueous layer was extracted with two portions of ethyl acetate. The combined organics were washed sequentially with saturated aqueous sodium bicarbonate solution and brine, dried over sodium sulfate and concentrated to give a brown solid. The solid was boiled in 2 L of hexane with charcoal, filtered, and concentrated in vacuo to give the title compound as a yellow solid. LC-MS 328 (M+1).

Step C: 2-(Trifluoromethyl)-5,6,7,8-tetrahydropyrido[3,4-d]pyrimidine, hydrochloride A flask containing a solution of 23.4 g (71.41 mmol) of 7-benzyl-4-chloro-2-(trifluoromethyl)-5,6,7,8-tetrahydropyrido[3,4-d]pyrimidine in 285 mL of ethyl acetate and 530 mL of methanol was purged with nitrogen, and 2 g of 10% Pd/C was added. The mixture was stirred under 1 atm of hydrogen until the reaction was judged complete by TLC analysis (about 7.5 h total). The mixture was filtered through Celite, and the Celite washed with methanol. The organics were concentrated in vacuo and the resultant pale yellow oil was triturated with 400 mL of ether. Crystals formed and an additional 400 mL of ether was added. The mixture was stirred overnight. The resultant solid was collected by filtration and dried in vacuo to give off-white crystals that contained an impurity by TLC analysis. The crystals were dissolved in a minimum amount of methanol. Ether was added to turbidity and the mixture was warmed on a steam bath. Crystals formed and the mixture was allowed to cool to ambient temperature and aged for 30 min. It was then filtered. The collected solid was dried in vacuo to give the title compound as a white crystalline solid. LC-MS 204 (M+1).

Step D: tert-Butyl 2-(trifluoromethyl)-5,8-dihydropyrido[3,4-d]pyrimidine-7(6H)-carboxylate To a solution of 600 mg (2.5 mmol) of 2-(trifluoromethyl)-5,6,7,8-tetrahydropyrido[3,4-d]pyrimidine hydrochloride and 0.883 mL (5 mmol) of N,N-diisopropylethylamine in 10 mL of dichloromethane, stirred in an ice bath under protection from moisture, was added 676 mg (3 mmol) of di-tert-butyl dicarbonate. The ice bath was removed, and the solution was stirred at room temperature for 2.5 h. The solvent was removed by rotary evaporation, and the residue was purified by flash chromatography on silica gel (10-30% ethyl acetate in hexanes) to give the title compound as a colorless oil. LC-MS 304 (M+1).

Step E: tert-Butyl 8-oxo-2-(trifluoromethyl)-5,8-dihydropyrido[3,4-d]pyrimidine-7(6H)-carboxylate To a mixture of 51 mg (0.328 mmol) of ruthenium dioxide and 25.9 mL (11.9 mmol) of 10% sodium periodate aqueous solution was added a solution of 766 mg (2.53 mmol) of tert-butyl 2-(trifluoromethyl)-5,8-dihydropyrido[3,4-d]pyrimidine-7(6H)-carboxylate in 20 mL of ethyl acetate. The mixture was stirred vigorously for 4 h and then partitioned between ethyl acetate and water. The aqueous phase was extracted with 2 additional portions of ethyl acetate. The combined organic fractions were concentrated. Flash chromatography of the residue on silica gel (9:1 hexanes/ethyl acetate) afforded material that was collected on a filter and washed with diethyl ether to give the title compound as a white solid. LC-MS 318 (M+1).

Step F: 2-(Trifluoromethyl)-6,7-dihydropyrido[3,4-d]pyrimidin-8(5H)-one

Approximately 485 mg (1.53 mmol) of tert-butyl 8-oxo-2-(trifluoromethyl)-5,8-dihydropyrido[3,4-d]pyrimidine-7(6H)-carboxylate was treated with 10 mL of 4M HCl in anhydrous dioxane, and the solution was stirred at room temperature for 0.5 h, then concentrated to dryness. The residue was washed with diethyl ether and dried to give the title compound as a white solid. LC-MS 218 (M+1).

Step G: 8-Methoxy-2-(trifluoromethyl)-5,6-dihydropyrido[3,4-d]pyrimidine

To a vigorously stirred mixture of 336 mg (1.33 mmol) of 2-(trifluoromethyl)-6,7-dihydropyrido[3,4-d]pyrimidin-8

(5H)-one and 2.94 g (27.7 mmol) of anhydrous sodium carbonate in 15 mL of dichloromethane was added 979 mg (6.6 mmol) of trimethyloxonium tetrafluoroborate. Vigorous stirring was continued at room temperature for 5.5 h. Then 15 mL of water was added, and the mixture was shaken. After separation of the phases, the aqueous layer was extracted twice with dichloromethane. The combined organic fractions were dried over sodium sulfate, filtered, and concentrated. Purification of the residue by flash chromatography on silica gel (0-2% methanol in dichloromethane) yielded the title compound as a yellow solid. LC-MS 232 (M+1).

INTERMEDIATE 6

3-(Trifluoromethyl)-6,7-dihydro[1,2,4]triazolo[4,3-a]pyrazine-8(5H)-thione

Step A: 3-(Trifluoromethyl)-1,2,4-triazolo[4,3-a]pyrazine

A sample of 2-hydrazinopyrazine was prepared from 2-chloropyrazine and hydrazine using a procedure analogous to that described in the literature [P. J. Nelson and K. T. Potts, J. Org. Chem., 27, 3243 (1962)], except that the crude product was extracted into 10% methanol/dichloromethane and filtered, and the filtrate was concentrated and purified by flash chromatography on silica gel, eluting with 100% ethyl acetate followed by 10% methanol in dichloromethane. A mixture of 2-hydrazinopyrazine (820 mg, 7.45 mmol), trifluoroacetic acid (2.55 g, 22.4 mmol), and polyphosphoric acid (10 mL) was heated to 140° C. with stirring for 18 h. The solution was added to ice and neutralized by the addition of ammonium hydroxide. The aqueous solution was extracted three times with ethyl acetate, washed with brine, and dried over anhydrous magnesium sulfate. Concentration followed by flash chromatography (silica gel, 1:1 hexane:ethyl acetate, then 100% ethyl acetate) afforded the title compound as a solid.

$^1$H NMR (500 MHz, CDCl$_3$): δ 8.17~8.20 (m, 2H), 9.54 (s, 1H); C/MS 189 (M+1).

Step B: 3-(Trifluoromethyl)-5,6,7,8-tetrahydro-1,2,4-triazolo[4,3-a]pyrazine 3-(Trifluoromethyl)-1,2,4-triazolo[4,3-a]pyrazine (540 mg, 2.87 mmol, from Step A) was hydrogenated under atmospheric hydrogen with 10% Pd/C (200 mg) as a catalyst in ethanol (10 mL) at ambient temperature for 18 h. Filtration through Celite followed by concentration gave a dark colored oil. Dichloromethane was added to the above oil and the insoluble black precipitate was filtered off. Concentration of the filtrate gave the title compound as an oil.

$^1$H NMR (500 MHz, CDCl$_3$) δ 2.21 (br, 1H), 3.29 (t, 2H, J=5.5 Hz), 4.09 (t, 2H, J=5.5 Hz), 4.24 (s, 2H); LC-MS 193 (M+1).

Step C: tert-Butyl 3-(trifluoromethyl)-5,6-dihydro[1,2,4]triazolo[4,3-a]pyrazine-7(8H)-carboxylate The title compound was prepared from 3-(trifluoromethyl)-5,6,7,8-tetrahydro-1,2,4-triazolo[4,3-a]pyrazine and di-tert-butyl dicarbonate by a procedure analogous to that used for Intermediate 5, Step D. LC-MS 293 (M+1).

Step D: tert-Butyl 8-oxo-3-(trifluoromethyl)-5,6-dihydro[1,2,4]triazolo[4,3-a]pyrazine-7(8H)-carboxylate By the procedure used for Intermediate 5, Step E, the title compound was obtained from tert-butyl 3-(trifluoromethyl)-5,6-dihydro[1,2,4]triazolo[4,3-a]pyrazine-7(8H)-carboxylate as a gray solid. LC-MS 307 (M+1).

Step E: 3-(Trifluoromethyl)-6,7-dihydro[1,2,4a]triazolo[4,3-a]pyrazin-8(5H)-one

The title compound was prepared as a gray solid from tert-butyl 8-oxo-3-(trifluoromethyl)-5,6-dihydro[1,2,4]triazolo[4,3-a]pyrazine-7(8H)-carboxylate according to the procedure used for Intermediate 5, Step F. LC-MS 207 (M+1).

Step F: 3-(Trifluoromethyl)-6,7-dihydro[1,2,4]triazolo[4,3-a]pyrazine-8(5H)-thione A mixture of 173 mg (0.84 mmol) of 3-(trifluoromethyl)-6,7-dihydro[1,2,4]triazolo[4,3-a]pyrazin-8(5H)-one, 703 mg (1.68 mmol) of Lawesson's Reagent, and 18 mL of xylenes was stirred at reflux for 4.5 h. After being cooled to room temperature, the solvent was decanted off, and the residue was washed with diethyl ether. The resulting solid was dried and purified by flash chromatography (20-50% acetone in hexanes) to give the title compound as a greenish-yellow solid. LC-MS 223 (M+1).

INTERMEDIATE 7

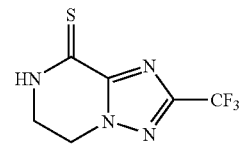

2-(Trifluoromethyl)-6,7-dihydro[1,2,4]triazolo[1,5-a]pyrazine-8(5H)-thione

Step A: 2,2,2-Trifluoro-N-pyrazin-2-ylacetamide

To a slightly heterogeneous solution of aminopyrazine (22.74 g, 239 mmol) and triethylamine (36.66 mL, 263 mmol) in dichloromethane (400 mL) was added trifluoroacetic anhydride (50.20 g, 239 mmol) dropwise at 0° C. The solution was stirred at 0° C. for 1 h and at ambient temperature for 2 h. Filtration of the resultant white precipitate followed by washing with dichloromethane afforded the title compound as a white solid.

$^1$H NMR (500 MHz, CD$_3$OD): δ 8.44-8.46 (m, 2H), 9.33 (d, 1H, J=1.4 Hz); LC/MS 192 (M+1).

Step B: 2,2,2-Trifluoro-N'-hydroxy-N-pyrazin-2-ylethanimidamide

To a suspension of 2,2,2-trifluoro-N-pyrazin-2-ylacetamide (14.56 g, 76.26 mmol, from Step A) in dichloroethane (325 mL) was added phosphorous pentachloride (421.73 g, 99.13 mmol) portionwise. The mixture was refluxed for 5 h. After evaporation of dichloroethane, the residue was suspended in tetrahydrofuran (325 mL). To the above mixture was added 50% aqueous hydroxylamine (20 mL) dropwise. After stirring at ambient temperature for 2 h, the mixture was partitioned between ethyl acetate and aqueous sodium bicarbonate. The aqueous layer was extracted three times with ethyl acetate. The combined organic layers were washed with brine and dried over anhydrous magnesium sulfate. Concentration gave the title compound as a yellow solid.

$^1$H-NMR (500 MHz, CD$_3$OD): δ 8.04 (m, 2H), 8.17 (s, 1H); LC/MS 207 (M+1).

Step C: 2-(Trifluoromethyl)[1,2,4]triazolo[1,5-a]pyrazine

A mixture of 2,2,2-trifluoro-N'-hydroxy-N-pyrazin-2-ylethanimidamide (10.5 g, 50.97 mmol, from Step B) and polyphosphoric acid (80 mL) was heated to 150° C. with stirring for 18 h. The solution was added to ice and neutralized by addition of ammonium hydroxide. The dark aqueous solution was extracted three times with ethyl acetate, washed with brine, and dried over anhydrous magnesium sulfate. Concentration followed by flash chromatography (1:1 hexane:ethyl acetate and then 100% ethyl acetate) afforded the title compound as a yellow solid.

$^1$H-NMR (500 MHz, CDCl$_3$): δ 8.42 (d, 1H, J=4.6 Hz), 8.67 (dd, 1H, J=1.4 and 4.6 Hz), 9/47 (d, 1H, J=1.4 Hz); LC/MS 189 (M+1).

Step D: 2-(Trifluoromethyl)-5,6,7,8-tetrahydro[1,2,4]triazolo[1,5-a]pyrazine 2-(Trifluoromethyl)[1,2,4]triazolo[1,5-a]pyrazine (340 mg, 1.81 mmol, from Step C) was hydrogenated under atmospheric hydrogen with 10% palladium on carbon (60 mg) as a catalyst in ethanol (10 mL) at ambient temperature for 18 h. Filtration through Celite followed by concentration gave a dark colored oil. Flash chromatography (100% ethyl acetate, then 10% methanol/dichloromethane) gave the title compound as a white solid.

$^1$H-NMR (500 MHz, CDCl$_3$): δ 1.80 (br, 1H), 3.40 (t, 2H, J=5.5 Hz), 4.22-4.26 (m, 4H); LC/MS 193 (M+1).

Step E: tert-Butyl 2-(trifluoromethyl)-5,6-dihydro[1,2,4]triazolo[1,5-a]pyrazine-7(8H)-carboxylate The title compound was prepared from 2-(trifluoromethyl)-5,6,7,8-tetrahydro[1,2,4]triazolo[1,5-a]pyrazine and di-tert-butyl dicarbonate by a procedure analogous to that used for Intermediate 5, Step D. LC/MS 293 (M+1).

Step F: tert-Butyl 8-oxo-2-(trifluoromethyl)-5,6-dihydro[1,2,4]triazolo[1,5-a]pyrazine-7(8H)-carboxylate By the procedure used for Intermediate 5, Step E, the title compound was prepared from tert-butyl 2-(trifluoromethyl)-5,6-dihydro[1,2,4]triazolo[1,5-a]pyrazine-7(8H)-carboxylate as a gray solid. LC-MS 307 (M+1).

Step G: 2-(Trifluoromethyl)-6,7-dihydro[1,2,4]triazolo[1,5-a]pyrazin-8(5H)-one By the procedure used for Intermediate 5, Step F, the title compound was prepared from tert-butyl 8-oxo-2-(trifluoromethyl)-5,6-dihydro[1,2,4]triazolo[1,5-a]pyrazine-7(8H)-carboxylate as a pale yellow solid. LC-MS 207 (M+1).

Step H: 2-(Trifluoromethyl)-6,7-dihydro[1,2,4]triazolo[1,5-a]pyrazine-8(5H)-thione By the procedure used for Intermediate 6, Step F, the title compound was prepared from 2-(trifluoromethyl)-6,7-dihydro[1,2,4]triazolo[1,5-a]pyrazin-8(5H)-one as a yellow solid. LC-MS 223 (M+1).

INTERMEDIATE 8

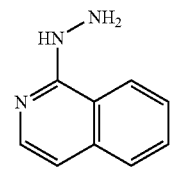

1-Hydrazinoisoquinoline

The title compound was prepared according to the procedure of J. Druey, U.S. Pat. No. 2,719,158 (1955). LC-MS 160 (M+1).

INTERMEDIATE 9

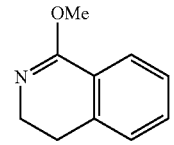

1-Methoxy-3,4-dihydroisoquinoline

The title compound was prepared from 3,4-dihydroisoquinolin-1(2H)-one [X.-J. Wang et al., *Tetrahedron Lett.*, 39, 6609 (1998)] according to the method of Intermediate 5, Step G. LC-MS 162 (M+1).

INTERMEDIATE 10

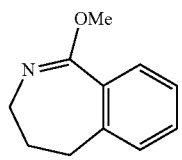

1-Methoxy-4,5-dihydro-3H-2-benzazepine

The title compound was prepared from 2,3,4,5-tetrahydro-1H-2-benzazepin-1-one [A. I. Meyers et al., *Tetrahedron*, 49, 1807 (1993)] according to the method of Intermediate 5, Step G.

LC-MS 176 (M+1).

INTERMEDIATE 11

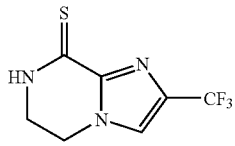

2-(Trifluoromethyl)-6,7-dihydroimidazo[1,2-a]pyrazine-8(5H)-thione

Step A: 2-(Trifluoromethyl)imidazo[1,2-a]pyrazine

To a solution of 2-aminopyrazine (5.25 g, 55.2 mmol) in ethanol (120 mL) was added 1-bromo-3,3,3-trifluoroacetone (5.73 mL, 55.2 mmol). The reaction was stirred at reflux for 20 h. After evaporation of solvent, the residue was partitioned between ethyl acetate and saturated aqueous sodium bicarbonate solution. The aqueous layer was extracted three times with ethyl acetate. The combined organic phase was washed with brine, dried over magnesium sulfate and concentrated. The residue was purified by flash chromatography (silica gel, 1:1 ethyl acetate:hexane, then 100% ethyl acetate) to give the title compound as a solid.

$^1$H NMR (500 MHz, CDCl$_3$): δ8.02 (m, 2H), 8.13(m, 1H), 9.22 (s, 1H); LC-MS 188 (M+1).

Step B: 2-(Trifluoromethyl)-5,6,7,8-tetrahydroimidazo[1,2-a]pyrazine

To a solution of 2-(trifluoromethyl)imidazo[1,2-a]pyrazine (2.0 g, 10.46 mmol, from Step A) in methanol (100 mL) was added 10% palladium on carbon (400 mg). The mixture was stirred under atmospheric hydrogen at ambient temperature for 14 h. The mixture was filtered through Celite and washed with methanol (3×). The filtrate was concentrated and purified by flash chromatography (silica gel, 10% methanol in ethyl acetate, then 15% methanol in chloroform with 1% aqueous ammonium hydroxide) to give the title compound as a solid.

$^1$H NMR (500 MHz, CDCl$_3$): δ1.93 (bs, 1H), 3.26 (t, 2H, J=5.5 Hz), 3.99 (t, 2H, J=5.5 Hz), 4.10 (s, 1H), 7.16 (s, 1H); LC-MS 192 (M+1).

Step C: 2-(Trifluoromethyl)-6,7-dihydroimidazo[1,2-a]pyrazine-8(5H)-thione

A mixture of 800 mg (4.18 mmol) of 2-(trifluoromethyl)-5,6,7,8-tetrahydroimidazo[1,2-a]pyrazine, 3.36 g of sulfur, and 4 mL of pyridine was stirred at reflux for 3 days and then concentrated to dryness. The residue was triturated with some chloroform to remove impurity and then purified by flash chromatography on silica gel (98:2:0.2 dichloromethane:methanol:concentrated ammonium hydroxide followed by 97:3:0.3 dichloromethane:methanol:concentrated ammonium hydroxide) to give the title compound as a yellow-orange solid. LC-MS 222 (M+1).

INTERMEDIATE 12

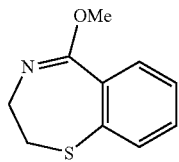

5-Methoxy-2,3-dihydro-1-benzothiepine

The title compound was prepared from commercial 3,4-dihydro-1-benzothiepin-5(2H)-one by the procedure used for Intermediate 5, Step G. LC-MS 194 (M+1).

INTERMEDIATE 13

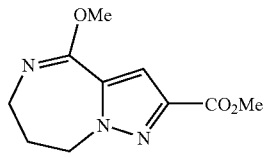

Methyl 4-methoxy-7,8-dihydro-6H-pyrazolo[1,5-a][1,4]diazepine-2-carboxylate

The title compound was prepared from commercial methyl 4-oxo-5,6,7,8-tetrahydro-4H-pyrazolo[1,5-a][1,4]diazepine-2-carboxylate by the procedure used for Intermediate 5, Step G.

LC-MS 224 (M+1).

INTERMEDIATE 14

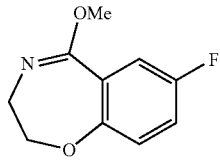

7-Fluoro-5-methoxy-2,3-dihydro-1,4-benzoxazepine

By the procedure used for Intermediate 5, Step G, the title compound was prepared from commercial 7-fluoro-3,4-dihydro-1,4-benzoxazepin-5(2H)-one. LC-MS 196 (M+1).

INTERMEDIATE 15

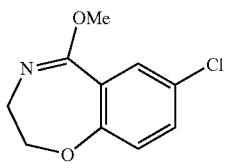

7-Chloro-5-methoxy-2,3-dihydro-1,4-benzoxazepine

By the procedure used for Intermediate 5, Step G, the title compound was prepared from commercial 7-chloro-3,4-dihydro-1,4-benzoxazepin-5(2H)-one. LC-MS 212 (M+1).

INTERMEDIATE 16

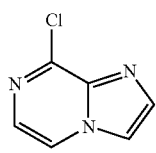

8-Chloroimidazo[1,2-a]pyrazine

The title compound was prepared by the procedure of W. C. Lumma, Jr., et al., *J. Med. Chem.*, 26, 357 (1983).

INTERMEDIATE 17

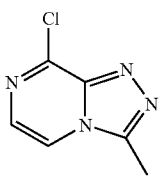

8-Chloro-3-methyl[1,2,4]triazolo[4,3-a]pyrazine

The title compound was prepared by the procedure of T. Huynh-Dinh et al., *J. Org. Chem.*, 44, 1028 (1979).

INTERMEDIATE 18

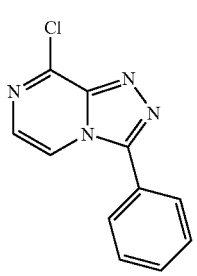

8-Chloro-3-phenyl[1,2,4]triazolo[4,3-a]pyrazine

As for Intermediate 17, the general method of T. Huynh-Dinh et al., *J. Org. Chem.*, 44, 1028 (1979) was used, except that trimethyl orthobenzoate was substituted for the orthoacetate. The precipitated solid was recrystallized from ethanol to give the title compound. LC-MS 231 (M+1).

INTERMEDIATE 19

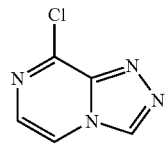

8-Chloro[1,2,4]triazolo[4,3-a]pyrazine

The title compound was prepared by the procedure of T. Huynh-Dinh et al., *J. Org. Chem.*, 44, 1028 (1979).

INTERMEDIATE 20

5-Hydrazino[1,2,4]triazolo[1,5-c]pyrimidine

A solution of 155 mg (1 mmol) of 5-chloro[1,2,4]triazolo[1,5-c]pyrimidine [D. J. Brown and K. Shinozuka, *Aust. J. Chem.*, 33, 1147 (1980)] in 6 mL of dry ethanol was added gradually to a vigorously stirred solution of 198 mg (204 mg, 4 mmol) of hydrazine monohydrate in 2 mL of dry ethanol. A white precipitate separated during the addition. After 1.5 h, the solid was collected on a filter. It was suspended in 2 mL of concentrated ammonium hydroxide and agitated for a few minutes. The solid was then collected on a filter and washed with some additional concentrated ammonium hydroxide, then with some ethanol, and finally with a large volume of diethyl ether. After drying, the title compound was obtained as a white solid, mp 245-246° C. (decomposition). LC-MS 151 (M+1).

INTERMEDIATES 21 AND 22

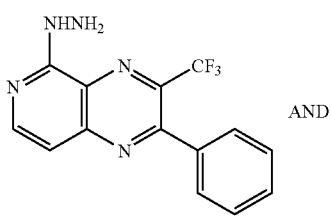

AND

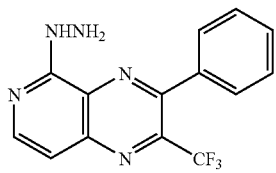

5-Hydrazino-2-phenyl-3-(trifluoromethyl)pyrido[3,4-b]pyrazine and 5-Hydrazino-3-phenyl-2-(trifluoromethyl)pyrido[3,4-b]pyrazine Step A: 5-Chloro-2-phenyl-3-(trifluoromethyl)pyrido[3,4-b]pyrazine and 5-Chloro-3-phenyl-2-(trifluoromethyl)pyrido[3,4-b]pyrazine A mixture of 500 mg (3.48 mmol) of 2-chloropyridine-3,4-diamine [H. Dvorakova et al., *Collect. Czech. Chem. Commun.*, 58, 629 (1993)], 718 mg (3.48 mmol) of 3,3,3-trifluoro-1-phenylpropane-1,2-dione hydrate, and 10 mL of ethanol was stirred at reflux for 4 h. Upon cooling, precipitation occurred. The solid was collected on a filter and washed with cold ethanol to give one regioisomer of the titled compounds (major product). The filtrate was concentrated to dryness, and the residue was flash chromatographed on silica gel (10-30% ethyl acetate in hexanes) to afford the other regioisomer of the titled compounds (minor product). It was not determined which structure corresponds to which regioisomer. LC-MS 310 (M+1) for both regioisomers.

Step B: 5-Hydrazino-2-phenyl-3-(trifluoromethyl)pyrido[3,4-b]pyrazine and 5-Hydrazino-3-phenyl-2-(trifluoromethyl)pyrido[3,4-b]pyrazine A 110 mg (0.355 mmol) sample of one regioisomer, corresponding either to 5-chloro-2-phenyl-3-(trifluoromethyl)pyrido[3,4-b]pyrazine or 5-chloro-3-phenyl-2-(trifluoromethyl)pyrido[3,4-b]pyrazine was stirred with 4.5 mL of hydrazine hydrate at room temperature for 5 min. The reaction mixture was then concentrated to dryness, and the residue was partitioned between dichloromethane and saturated sodium bicarbonate aqueous solution. The organic phase was dried over sodium sulfate, filtered, and concentrated to give one regioisomer of the titled compounds as a pale green solid. The other regioisomer was obtained similarly. It was not determined which structure corresponds to which regioisomer. LC-MS 306 (M+1) for both regioisomers.

INTERMEDIATE 23

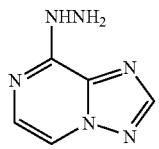

8-Hydrazino[1,2,4]triazolo[1,5-a]pyrazine

The title compound was prepared according to the procedure of B. Verček et al., *Tetrahedron Lett.*, 4539 (1974).

INTERMEDIATES 24 AND 25

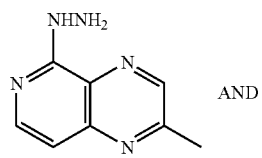

AND

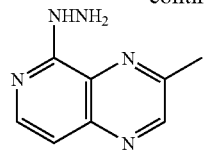

5-Hydrazino-2-methylpyrido[3,4-b]pyrazine and 5-Hydrazino-3-methylpyrido[3,4-b]pyrazine The two regioisomeric title compounds were made according to the procedures described for Intermediates 21 and 22. It was not determined which structure corresponds to which regioisomer.
LC-MS 176 (M+1) for both regioisomers.

INTERMEDIATES 26 AND 27

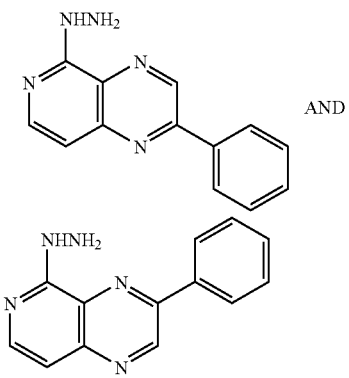

5-Hydrazino-2-phenylpyrido[3,4-b]pyrazine and 5-Hydrazino-3-phenylpyrido[3,4-b]pyrazine The two regioisomeric title compounds were made according to the procedures described for Intermediates 21 and 22. It was not determined which structure corresponds to which regioisomer.
LC-MS 238 (M+1) for both regioisomers.

INTERMEDIATE 28

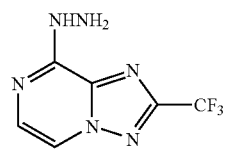

8-Hydrazino-2-(trifluoromethyl)[1,2,4]triazolo[1,5-a]pyrazine

Step A: 5-Bromo-2-(trifluoromethyl)[1,2,4]triazolo[1,5-a]pyrazine, hydrobromide

A solution of 500 mg (2.66 mmol) of 2-(trifluoromethyl)[1,2,4]triazolo[1,5-a]pyrazine (Intermediate 7, Step C) in 2.5 mL of dry ethanol, stirred at 0° C. under protection from moisture, was treated dropwise with 0.151 mL (2.92 mmol) of bromine. After 20 minutes at 0° C., the solution was concentrated and dried to give the title compound as an orange solid. LC-MS 267, 269 (M+1).

Step B: 8-Hydrazino-2-(trifluoromethyl)[1,2,4]triazolo[1,5-a]pyrazine

A solution of 400 mg (1.15 mmol) of 5-bromo-2-(trifluoromethyl) [1,2,4]triazolo[1,5-a]pyrazine hydrobromide in 2.5 mL of dry ethanol was treated dropwise with 0.799 mL (11.5 mmol) of hydrazine hydrate, and stirring was continued at ambient temperature overnight. The reaction mixture was concentrated to dryness, and the residue was extracted with dichloromethane and then with tetrahydrofuran. The organic extracts were washed with saturated sodium bicarbonate aqueous solution, filtered, and concentrated. Purification of the residue by preparative HPLC (C18 reverse phase column, 10-60% acetonitrile in water containing 0.05% trifluoroacetic acid) afforded the title compound as a yellow solid. LC-MS 219 (M+1).

INTERMEDIATE 29

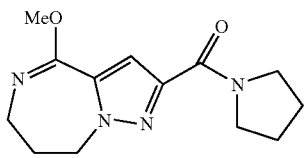

4-Methoxy-2-(pyrrolidin-1-ylcarbonyl)-7,8-dihydro-6H-pyrazolo[1,5-a][1,4]diazepine Step A: 2-(Pyrrolidin-1-ylcarbonyl)-5,6,7,8-tetrahydro-4H-pyrazolo[1,5-a][1,4]diazepin-4-one A mixture of 200 mg (1.03 mmol) of commercial 2-(pyrrolidin-1-ylcarbonyl)-5,6,7,8-tetrahydro-4H-pyrazolo[1,5-a][1,4]diazepin-4-one, 0.258 mL (3.09 mmol) of pyrrolidine, 467 mg (1.24 mmol) of O-(7-azabenzotriazol-1-yl)-N,N,N'N'-tetramethyluronium hexafluorophosphate (HATU), 212 mg (1.55 mmol) of 1-hydroxy-7-azabenzotriazole (HOAT), 0.451 mL (2.58 mmol) of N,N-diisopropylethylamine, and 10 mL of anhydrous dichloromethane was stirred at room temperature overnight and then concentrated to dryness. Flash chromatography of the residue on silica gel (5-30% methanol in dichloromethane) provided the title compound as a light yellow gum. LC-MS 249 (M+1).

Step B: 4-Methoxy-2-(pyrrolidin-1-ylcarbonyl)-7,8-dihydro-6H-pyrazolo[1,5-a][1,4]diazepine This material was obtained by use of the procedure for Intermediate 5, Step G. Purification of the crude product by flash chromatography on silica gel (3-10% methanol in dichloromethane) followed by preparative thin-layer chromatography on silica gel (93:7 dichloromethane:methanol) afforded the title compound as a pale yellow, tacky solid. LC-MS 263 (M+1).

INTERMEDIATE 30

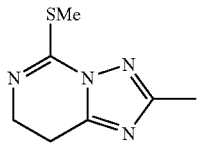

2-Methyl-5-(methylthio)-7,8-dihydro[1,2,4]triazolo[1,5-c]pyrimidine

Step A: 2-Methyl-7,8-dihydro[1,2,4]triazolo[1,5-c]pyrimidine-5(6H)-thione

A solution of 1.99 g (10 mmol) of 2-(5-methyl-1,2,4-triazol-3-yl)ethanamine dihydrochloride in a mixture of 13 mL of water and 7 mL (35 mmol) of 5N sodium hydroxide aqueous solution was stirred under nitrogen at room temperature as a solution of 5.4 mL of carbon disulfide in 30 mL of dry ethanol was added dropwise over about 30 minutes. After 5 h, the excess carbon disulfide was removed by rotary evaporation. The resulting solution was stirred under nitrogen at room temperature as 1.08 mL (1.23 g, 11 mmol) of ethyl chloroformate was added dropwise over about 10 minutes. Stirring at room temperature was continued overnight. The solution was partially concentrated to remove the ethanol, resulting in precipitation. The pH was made slightly acidic by addition of acetic acid. Then the solid was collected on a filter, washed with a small volume of water, and dried to give the title compound as a solid. LC-MS 169 (M+1).

Step B: 2-Methyl-5-(methylthio)-7,8-dihydro[1,2,4]triazolo[1,5-c]pyrimidine

A suspension of 505 mg (3 mmol) of 2-methyl-7,8-dihydro[1,2,4]triazolo[1,5-c]pyrimidine-5(6H)-thione in 12 mL of 50% sodium hydroxide (aqueous) was treated with 0.187 mL (426 mg, 3.3 mmol) of iodomethane. The mixture was stirred vigorously at room temperature in a stoppered flask. After 2 h, the mixture was partitioned between 25 mL of dichloromethane and 12 mL of water (CAUTION: exotherm upon addition of water). The organic phase was separated, and the aqueous phase was re-extracted with an additional 5 mL of dichloromethane. The combined organic fractions were dried over magnesium sulfate, filtered, and concentrated to dryness. The residue was flash chromatographed on silica gel (99:1 dichloromethane:methanol) to yield the title compound as white crystals, mp 75.5-76.5° C. LC-MS 183 (M+1).

INTERMEDIATES 31 AND 32

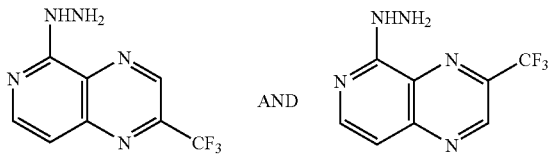

5-Hydrazino-2-(trifluoromethyl)pyrido[3,4-b]pyrazine and 5-Hydrazino-3-(trifluoromethyl)pyrido[3,4-b]pyrazine Step A: 5-Chloro-2-(trifluoromethyl)pyrido[3,4-b]pyrazine and 5-Chloro-3-(trifluoromethyl)pyrido[3,4-b]pyrazine A mixture of 2.00 g (7.41 mmol) of 1,1-dibromo-3,3,3-trifluoroacetone, 2.42 g (29.6 mmol) of sodium acetate, and 1.5 mL of water was stirred at reflux for 30 min and then cooled. To this was added a solution of 532 mg (3.71 mmol) of 2-chloropyridine-3,4-diamine [H. Dvorakova et al., Collect. Czech. Chem. Commun., 58, 629 (1993)] in 8 mL of ethanol, and the resulting mixture was stirred at reflux for an additional 5 h. The cooled reaction mixture was concentrated to dryness. Because of partial hydrolysis, the residue was treated with an excess of phosphorus oxychloride, and the resulting mixture was stirred at reflux overnight. The cooled solution was poured over ice. After most of the ice had melted, the mixture was neutralized by cautious addition of sodium carbonate. After gas evolution had subsided, the product was extracted with dichloromethane. The organic phase was dried over sodium sulfate, filtered, and concentrated. The residue was flash chromatographed on silica gel (0-30% ethyl acetate in hexanes), resulting in separation and isolation of two regioisomers corresponding to the titled compounds. It was not determined which structure corresponds to which regioisomer.

LC-MS 234 (M+1) for both regioisomers.

Step B: 5-Hydrazino-2-(trifluoromethyl)pyrido[3,4-b]pyrazine and 5-Hydrazino-3-(trifluoromethyl)pyrido[3,4-b]pyrazine By the procedure used for Intermediates 21 and 22, Step B, the two regioisomeric chloro compounds from Step A, above, were separately converted to the title compounds. It was not determined which structure corresponds to which regioisomer. LC-MS 230 (M+1) for both regioisomers.

INTERMEDIATE 33

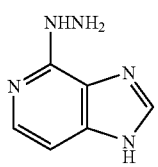

4-Hydrazino-1H-imidazo[4,5-c]pyridine

A mixture of 200 mg (1.3 mmol) of 4-chloro-1H-imidazo[4,5-c]pyridine [J. A. Montgomery and K. Hewson, *J. Med. Chem.*, 8, 708 (1965)], 0.253 mL (261 mg, 5.2 mmol) of hydrazine hydrate, and 5 mL of ethanol was stirred at room temperature overnight. The precipitate was collected on a filter, washed with a little ethanol, and dried to give the title compound as a solid. LC-MS 150 (M+1).

INTERMEDIATE 34

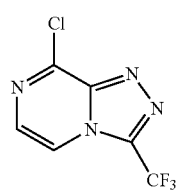

8-Chloro-3-(trifluoromethyl)[1,2,4]triazolo[4,3-a]pyrazine

Step A: 3-(Trifluoromethyl)[1,2,4]triazolo[4,3-a]pyrazine 7-oxide

A mixture of 250 mg (1.33 mmol) of 3-(trifluoromethyl)[1,2,4]triazolo[4,3-a]pyrazine (Intermediate 6, Step A), 0.479 mL (4.66 mmol) of 30% hydrogen peroxide aqueous solution, and 2 mL of glacial acetic acid was stirred at 95° C.

After 8 h, the solution was cooled and concentrated. The residue was partitioned between dichloromethane and saturated sodium bicarbonate aqueous solution. Thin-layer chromatography on silica gel (90:10:1 dichloromethane:methanol:concentrated ammonium hydroxide solution) revealed that the product was in the aqueous phase. Therefore, the aqueous solution was concentrated to dryness, and the residue was purified by preparative HPLC (C18 reverse phase column, 0-50% acetonitrile in water containing 0.05% trifluoroacetic acid) to provide the title compound as a white solid. LC-MS 205 (M+1).

Step B: 8-Chloro-3-(trifluoromethyl)[1,2,4]triazolo[4,3-a]pyrazine

A suspension of 40 mg (0.196 mmol) of 3-(trifluoromethyl)[1,2,4]triazolo[4,3-a]pyrazine 7-oxide in 0.9 mL of phosphorus oxychloride was stirred at reflux for 2.5 h. The cooled solution was concentrated to dryness. Purification of the residue by preparative HPLC (C18 reverse phase column, 10-70% acetonitrile in water containing 0.05% trifluoroacetic acid) and then by flash chromatography on silica gel (10-30% ethyl acetate in hexanes) yielded the title compound as a white solid. LC-MS 223 (M+1).

INTERMEDIATE 35

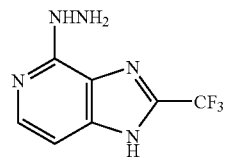

4-Hydrazino-2-(trifluoromethyl)-1H-imidazo[4,5-c]pyridine

Step A: 4-Chloro-2-(trifluoromethyl)-1H-imidazo[4,5-c]pyridine

A mixture of 400 mg (2.79 mmol) of 2-chloropyridine-3,4-diamine [H. Dvorakova et al., *Collect. Czech. Chem. Commun.*, 58, 629 (1993)] and a few mL of trifluoroacetic acid was stirred at reflux overnight. The cooled solution was concentrated and then re-concentrated from ethanol. Flash chromatography of the residue on silica gel [0-10% of (9:1 methanol:concentrated ammonium hydroxide solution) in dichloromethane] yielded the title compound as a foam. LC-MS 222 (M+1).

Step B: 4-Hydrazino-2-(trifluoromethyl)-1H-imidazo[4,5-c]pyridine

A mixture of 132 mg (0.6 mmol) of 4-chloro-2-(trifluoromethyl)-1H-imidazo[4,5-c]pyridine, 0.0787 mL (2.4 mmol) of anhydrous hydrazine, and 3 mL of ethanol was stirred at reflux for 2 days. The cooled, filtered solution was concentrated, and the residue was partitioned between ethyl acetate and water. The organic phase was dried over sodium sulfate, filtered and concentrated to yield the title compound. LC-MS 218 (M+1).

INTERMEDIATE 36

4-Hydrazino-1H-[1,2,3]triazolo[4,5-c]pyridine

The title compound was prepared according to the procedure of T. Talik and B. Brekiesz, *Rocz. Chem.*, 38, 887 (1964).

INTERMEDIATE 37

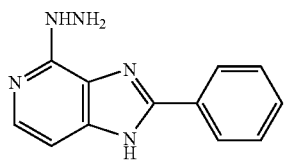

4-Hydrazino-2-phenyl-1H-imidazo[4,5-c]pyridine

Step A:
4-Chloro-2-phenyl-1H-imidazo[4,5-c]pyridine

A mixture of 100 mg (0.696 mmol) of 2-chloropyridine-3, 4-diamine [H. Dvorakova et al., *Collect. Czech. Chem. Commun.*, 58, 629 (1993)], 0.086 mL (0.835 mmol) of benzaldehyde, and 2 mL of nitrobenzene was heated at 175° C. under microwave irradiation for 30 min. The cooled solution was treated with 500 mg of Montmorillonite K 10 clay, and microwave irradiation at 175° C. was continued for an additional 30 min. The cooled mixture was filtered through Celite, and the filter cake was washed with methanol. The combined filtrate and washings were concentrated to dryness. Flash chromatography of the residue on silica gel (0-5% methanol in dichloromethane) yielded the title compound as a foam. LC-MS 230 (M+1).

Step B:
4-Hydrazino-2-phenyl-1H-imidazo[4,5-c]pyridine

A mixture of 130 mg (0.568 mmol) of 4-chloro-2-phenyl-1H-imidazo[4,5-c]pyridine, 0.110 mL (114 mg, 2.4 mmol) of hydrazine hydrate, and 3 mL of 2-methoxyethanol was stirred at reflux for 2 days. The cooled solution was concentrated, and the residue was partitioned between ethyl acetate and water. The organic phase was dried over sodium sulfate, filtered and concentrated to yield the title compound. LC-MS 226 (M+1).

INTERMEDIATE 38

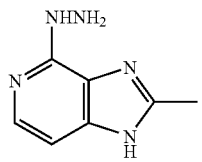

4-Hydrazino-2-methyl-1H-imidazo[4,5-c]pyridine

The title compound was prepared analogously to the procedures used for Intermediate 37.
LC-MS 164 (M+1).

INTERMEDIATE 39

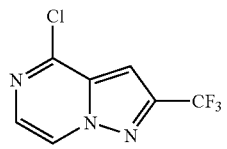

4-Chloro-2-(trifluoromethyl)pyrazolo[1,5-a]pyrazine

Step A: N-(2,2-Dimethoxyethyl)-3-(trifluoromethyl)-1H-pyrazole-5-carboxamide

A mixture of 500 mg (2.78 mmol) of 3-(trifluoromethyl)-1H-pyrazole-5-carboxylic acid, 0.333 mL (3.05 mmol) of aminoacetaldehyde dimethyl acetal, 588 mg (3.05 mmol) of 1-(3-dimethylaminopropyl)-3-ethylcarbodiimide hydrochloride (EDC), 510 mg (3.33 mmol) of 1-hydroxybenzotriazole (HOBT), 1.92 mL (11.1 mmol) of N,N-diisopropylethylamine, and 20 mL of dichloromethane was stirred at room temperature for 20 h and then concentrated. Purification of the residue by flash chromatography on silica gel (0-10% methanol in dichloromethane) afforded the title compound as a white solid. LC-MS 268 (M+1).

Step B: 2-(Trifluoromethyl)pyrazolo[1,5-a]pyrazin-4(5H)-one

A mixture of 267 mg (1 mmol) of N-(2,2-dimethoxyethyl)-3-(trifluoromethyl)-1H-pyrazole-5-carboxamide, 1.6 mL of trifluoroacetic acid, and 1.6 mL of dichloromethane was stirred at room temperature overnight and then concentrated. The residue was suspended in polyphosphoric acid (enough to cover it) and heated at 145° C. for 4.5 h. The cooled mixture was treated with ice, and the pH was adjusted to 8-9 by addition of concentrated ammonium hydroxide solution. The mixture was transferred to a separatory funnel and shaken with dichloromethane. The organic phase was separated, and the aqueous phase was extracted twice more with dichloromethane. The combined organic fractions were dried over sodium sulfate, filtered, and concentrated to yield the title compound as a solid.
LC-MS 204 (M+1).

Step C:
4-Chloro-2-(trifluoromethyl)pyrazolo[5-a]pyrazine

A mixture of 60 mg (0.295 mmol) of 2-(trifluoromethyl) pyrazolo[1,5-a]pyrazin-4(5H)-one, 0.149 mL (140 mg, 0.94 mmol) of N,N-diethylaniline, and 3 mL of phosphorus oxychloride was stirred at reflux for 15 h. The cooled solution was partitioned between ethyl acetate and 2N aqueous hydrochloric acid. The organic phase was washed with an additional portion of 2N aqueous hydrochloric acid and then with saturated sodium carbonate aqueous solution. The ethyl acetate solution was dried over sodium sulfate, filtered, and concentrated. Purification of the residue by flash chromatography on silica gel (5-20% ethyl acetate in hexanes) afforded the title compound as a pale yellow solid.

LC-MS 222 (M+1).

INTERMEDIATE 40

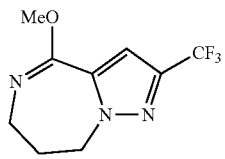

4-Methoxy-2-(trifluoromethyl)-7,8-dihydro-6H-pyrazolo[1,5-a][1,4]diazepine

Step A: N-(3-Bromopropyl)-3-(trifluoromethyl)-1H-pyrazole-5-carboxamide

To a solution of 500 mg (2.78 mmol) of 3-(trifluoromethyl)-1H-pyrazole-5-carboxylic acid, 682 mg (3.05 mmol) of 3-bromopropylamine hydrobromide, and 1.4 mL (1.04 g, 8.04 mmol) of N,N-diisopropylethylamine in 20 mL of dichloromethane were added 1.2 g (3.06 mmol) of O-(7-azabenzotriazol-1-yl)-N,N,N',N'-tetramethyluronium hexafluorophosphate (HATU) and 459 mg (3.38 mmol) of 1-hydroxy-7-azabenzotriazole (HOAT). After being stirred at room temperature for 45 min, the reaction mixture was partitioned between dichloromethane and saturated sodium carbonate aqueous solution. The organic phase was washed with 5% aqueous citric acid solution, then dried over sodium sulfate, and concentrated. The residue was leached with dichloromethane containing a little methanol. Concentration of the organic extract yielded the title compound. LC-MS 300, 302 (M+1).

Step B: 2-(Trifluoromethyl)-5,6,7,8-tetrahydro-4H-pyrazolo[1,5-a][1,4]diazepin-4-one A mixture of 400 mg (1.33 mmol) of N-(3-bromopropyl)-3-(trifluoromethyl)-1H-pyrazole-5-carboxamide, 350 mL (2 mmol) of N,N-diisopropylethylamine, and 8 mL of acetonitrile was stirred at reflux for 4.5 h. The cooled reaction mixture was concentrated, and the residue was flash chromatographed on silica gel [0-10% of (9:1 methanol:concentrated ammonium hydroxide) in dichloromethane]. Further purification by preparative HPLC (C18 reverse phase column, 10-50% acetonitrile in water containing 0.05% trifluoroacetic acid) separated the product from a major by-product, 2-[3-(trifluoromethyl)-1H-pyrazol-5-yl]-1,3-oxazinane, to give the title compound.

LC-MS 220 (M+1).

Step C: 4-Methoxy-2-(trifluoromethyl)-7,8-dihydro-6H-pyrazolo[1,5-a][1,4]diazepine By the procedure used for Intermediate 5, Step G, the title compound was obtained as an oil. LC-MS 234 (M+1).

INTERMEDIATE 41

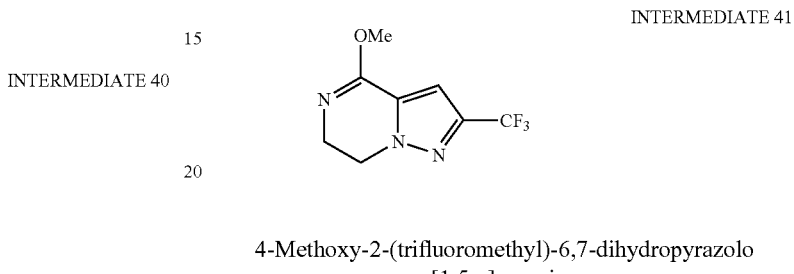

4-Methoxy-2-(trifluoromethyl)-6,7-dihydropyrazolo[1,5-a]pyrazine

The title compound was prepared following the procedures described for Intermediate 40, except that 2-(bromo)ethylamine hydrobromide was used in place of 3-(bromo)propylamine hydrobromide in the first step. LC-MS 220 (M+1).

INTERMEDIATE 42

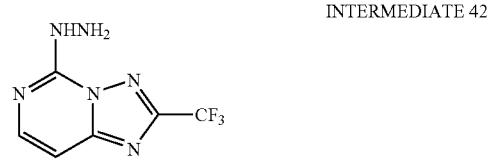

5-Hydrazino-2-(trifluoromethyl)[1,2,4]triazolo[1,5-c]pyrimidine

Step A: 2-(Trifluoromethyl)[1,2,4]triazolo[1,5-c]pyrimidin-5(6H)-one

A mixture of 631 mg (5 mmol) of 4-hydrazinopyrimidin-2(1H)-one [D. J. Brown and K. Shinozuka, Aust. J. Chem., 33, 1147 (1980)] and 4 mL of trifluoroacetic acid was stirred within a sealed tube at 100° C. for 40 h. The solution was concentrated, and the residue was triturated with diethyl ether. The resulting solid was collected on a filter, washed with some additional diethyl ether, and dried to afford the title compound as a very pale, grayish-tan solid, mp 203-205° C. LC-MS 205 (M+1).

Step B: 5-Chloro-2-(trifluoromethyl)[1,2,4]triazolo[1,5-c]pyrimidine

By the procedure of Intermediate 39, Step C, 2-(trifluoromethyl)[1,2,4]triazolo[1,5-c]pyrimidin-5(6H)-one was converted to the title compound as light green crystals, mp 47-48° C.

LC-MS 223 (M+1).

Step C: 5-Hydrazino-2-(trifluoromethyl)[1,2,4]triazolo[1,5-c]pyrimidine

By the procedure used for Intermediate 20, 5-chloro-2-(trifluoromethyl)-[1,2,4]triazolo[1,5-c]pyrimidine was converted to the title compound as white crystals, mp 161-162.5° C.
LC-MS 219 (M+1).

INTERMEDIATE 43

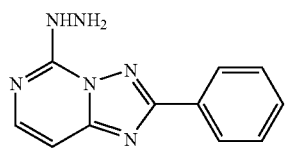

5-Hydrazino-2-phenyl[1,2,4]triazolo[1,5-c]pyrimidine

By the procedure used for Intermediate 20, 5-chloro-2-phenyl[1,2,4]triazolo[1,5-c]pyrimidine [D. J. Brown and K. Shinozuka, *Aust. J. Chem.*, 33, 1147 (1980)] was converted to the title compound as a white powder, mp 216-217.5° C. LC-MS 227 (M+1).

EXAMPLE 1

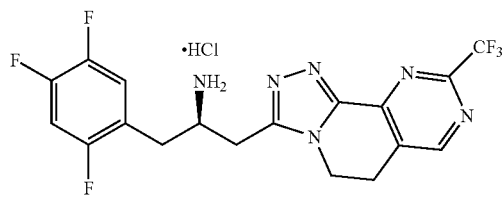

{(1R)-1-(2,4,5-Trifluorobenzyl)-2-[9-(trifluoromethyl)-5,6-dihydro[1,2,4]triazolo[4',3':1,2]pyrido[3,4-d]pyrimidin-3-yl]ethyl}amine, hydrochloride Step A: tert-Butyl((1R)-3-oxo-1-(2,4,5-trifluorobenzyl)-3-{2-[2-(trifluoromethyl)-5,6-dihydropyrido[3,4-d]pyrimidin-8-yl]hydrazino}propyl)carbamate A mixture of 150 mg (0.433 mmol) of tert-butyl[(1R)-3-hydrazino-3-oxo-1-(2,4,5-trifluorobenzyl)propyl]carbamate (Intermediate 4), 100 mg (0.433 mmol) of 8-methoxy-2-(trifluoromethyl)-5,6-dihydropyrido[3,4-d]pyrimidine (Intermediate 5) and 4 mL of anhydrous methanol was stirred at room temperature for 5.5 h and then diluted with diethyl ether. The solid was collected on a filter and dried to give the title compound. LC-MS 547 (M+1).

Step B: tert-Butyl{(1R)-1-(2,4,5-trifluorobenzyl)-2-[9-(trifluoromethyl)-5,6-dihydro[1,2,4]triazolo[4',3':1,2]pyrido[3,4-d]pyrimidin-3-yl]ethyl}carbamate A mixture of 63 mg (0.115 mmol) of tert-butyl((1R)-3-oxo-1-(2,4,5-trifluorobenzyl)-3-{2-[2-(trifluoromethyl)-5,6-dihydropyrido[3,4-d]pyrimidin-8-yl]hydrazino}propyl)carbamate and 2 mL of 2-methoxyethanol was stirred at reflux for 5.5 h and then concentrated. Purification of the residue by preparative HPLC (C18 reverse phase column, 30-80% acetonitrile in water containing 0.05% trifluoroacetic acid) afforded the title compound as a white solid. LC-MS 529 (M+1).

Step C: {(1R)-1-(2,4,5-Trifluorobenzyl)-2-[9-(trifluoromethyl)-5,6-dihydro[1,2,4]triazolo[4',3':1,2]pyrido[3,4-d]pyrimidin-3-yl]ethyl}amine, hydrochloride To 47 mg (0.89 mmol) of tert-butyl{(1R)-1-(2,4,5-trifluorobenzyl)-2-[9-(trifluoromethyl)-5,6-dihydro[1,2,4]triazolo[4',3':1,2]pyrido[3,4-d]pyrimidin-3-yl]ethyl}carbamate was added 1.8 mL of 4M HCl in anhydrous dioxane. The mixture was stirred at room temperature for 30 minutes and then concentrated. The residue was washed with diethyl ether and dried to give the title compound as a white solid. LC-MS 429 (M+1).

EXAMPLE 2

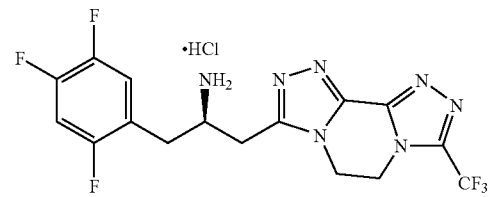

{(1R)-1-(2,4,5-Trifluorobenzyl)-2-[8-(trifluoromethyl)-5,6-dihydrobis[1,2,4]triazolo[3,4-c4', 3'-a]pyrazin-3-yl]ethyl}amine, hydrochloride Step A: tert-Butyl((1R)-3-oxo-1-(2,4,5-trifluorobenzyl)-3-{2-[3-(trifluoromethyl)-5,6-dihydro[1,2,4]triazolo[4,3-a]pyrazin-8-yl]hydrazino}propyl)carbamate A mixture of 207 mg (0.6 mmol) of tert-butyl[(1R)-3-hydrazino-3-oxo-1-(2,4,5-trifluorobenzyl)propyl]carbamate (Intermediate 4), 110 mg (0.5 mmol) of 3-(trifluoromethyl)-6,7-dihydro[1,2,4]triazolo[4,3-a]pyrazine-8(5H)-thione (Intermediate 6), and 5.5 mL of methanol was stirred at reflux for 1 day. Diethyl ether was added to the cooled solution, resulting in precipitation. The solid was removed by filtration, and the filtrate was concentrated to dryness. Purification of the residue by preparative HPLC (C18 reverse phase column, 30-80% acetonitrile in water containing 0.05% trifluoroacetic acid) afforded the title compound. LC-MS 536 (M+1).

Step B: tert-Butyl{(1R)-1-(2,4,5-trifluorobenzyl)-2-[8-(trifluoromethyl)-5,6-dihydrobis[1,2,4]triazolo[3,4-c:4',3'-a]pyrazin-3-yl]ethyl}carbamate The title compound was obtained from tert-butyl((1R)-3-oxo-1-(2,4,5-trifluorobenzyl)-3-{2-[3-(trifluoromethyl)-5,6-dihydro[1,2,4]triazolo[4,3-a]pyrazin-8-yl]hydrazino}propyl)carbamate by the procedure of Example 1, Step B. LC-MS 518 (M+1).

Step C: {(1R)-1-(2,4,5-Trifluorobenzyl)-2-[8-(trifluoromethyl)-5,6-dihydrobis[1,2,4]triazolo[3,4-c:4',3'-a]pyrazin-3-yl]ethyl}amine, hydrochloride The title compound was obtained from tert-butyl{(1R)-1-(2,4,5-trifluorobenzyl)-2-[8-(trifluoromethyl)-5,6-dihydrobis[1,2,4]triazolo[3,4-c:4',3'-a]pyrazin-3-yl]ethyl}carbamate by the procedure of Example 1, Step C. LC-MS 418 (M+1).

EXAMPLE 3

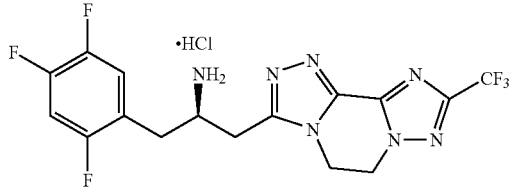

{(1R)-1-(2,4,5-Trifluorobenzyl)-2-[9-(trifluoromethyl)-5,6-dihydrobis[1,2,4]triazolo[1,5-a:3',4'-c]pyrazin-3-yl]ethyl}amine, hydrochloride Step A: {(1R)-1-(2,4,5-Trifluorobenzyl)-2-[9-(trifluoromethyl)-5,6-dihydrobis[1,2,4]triazolo[1,5-a:3',4'-c]pyrazin-3-yl]ethyl}amine A mixture of 208 mg (0.6 mmol) of of tert-butyl[(1R)-3-hydrazino-3-oxo-1-(2,4,5-trifluorobenzyl)propyl]carbamate (Intermediate 4), 100 mg (0.45 mmol) of 2-(trifluoromethyl)-6,7-dihydro[1,2,4]triazolo[1,5-a]pyrazine-8(5H)-thione (Intermediate 7), and 5 mL of 2-methoxyethanol was stirred at reflux for 18 h, resulting primarily in ring closure of the initial adduct as well as loss of the Boc group. The cooled solution was purified by preparative HPLC (C18 reverse phase column, 30-75% acetonitrile in water containing 0.05% trifluoroacetic acid) to afford the title compound. LC-MS 418 (M+1).

Step B: {(1R)-1-(2,4,5-Trifluorobenzyl)-2-[9-(trifluoromethyl)-5,6-dihydrobis[1,2,4]triazolo[1,5-a:3',4'-c]pyrazin-3-yl]ethyl}amine hydrochloride The {(1R)-1-(2,4,5-trifluorobenzyl)-2-[9-(trifluoromethyl)-5,6-dihydrobis[1,2,4]triazolo[1,5-a:3',4'-c]pyrazin-3-yl]ethyl}amine (free base) from Step A was treated an excess of 4M HCl in anhydrous dioxane, and the mixture was stirred at room temperature for 1 h. The residue obtained upon concentration of the reaction mixture was washed with ether and dried to afford the title compound as a white solid. LC-MS 418 (M+1).

EXAMPLE 4

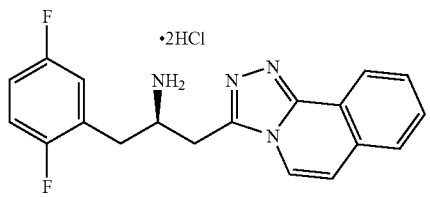

[(1R)-1-(2,5-Difluorobenzyl)-2-[1,2,4]triazolo[3,4-a]isoquinolin-3-ylethyl]amine, dihydrochloride Step A: tert-Butyl[(1R)-1-(2,5-difluorobenzyl)-3-(2-isoquinolin-1-ylhydrazino)-3-oxopropyl]carbamate A solution of 158 mg (0.5 mmol) of (3R)-3-[(tert-butoxycarbonyl)amino]-4-(2,5-difluorophenyl)butanoic acid (Intermediate 1), 96 mg (0.5 mmol) of 1-(3-dimethylaminopropyl)-3-ethylcarbodiimide hydrochloride (EDC) and 89 mg (0.63 mmol based on 95% purity) of 1-hydroxybenzotriazole (HOBT) in 4 mL of anhydrous dichloromethane was stirred at room temperature in a stoppered flask. After 15-20 min, this solution was added dropwise by syringe through a septum to a second solution of 95.5 mg (0.6 mmol) of 1-hydrazinoisoquinoline (Intermediate 8) and 0.261 mL (194 mg, 1.5 mmol) of N,N-diisopropylethylamine in 2 mL of anhydrous dichloromethane and 2 mL of anhydrous DMF. Stirring under nitrogen was continued for 4 h. The solution was then concentrated under vacuum. The residue was partitioned between ethyl acetate and 5% aqueous citric acid solution. The organic phase was washed with more 5% citric acid, then with water, and finally with saturated sodium carbonate aqueous solution. The organic solution was dried over magnesium sulfate, filtered and concentrated. The residue contained the title compound along with some material that had already undergone ring closure. LC-MS 457 (M+1 for title compound), 439 (M+1 for ring-closed product).

Step B: tert-Butyl[(1R)-1-(2,5-difluorobenzyl)-2-[1,2,4]triazolo[3,4-a]isoquinolin-3-ylethyl]carbamate The crude residue from Step A was treated with 5 mL of 2-methoxyethanol, and the mixture was stirred at reflux for 1 h. The residue obtained upon concentration was flash chromatographed on silica gel (1-2.5% methanol in dichloromethane) to provide the title compound as a light tan solid, mp 185-187° C. (decomposition). LC-MS 439 (M+1).

Step C: [(1R)-1-(2,5-Difluorobenzyl)-2-[1,2,4]triazolo[3,4-a]isoquinolin-3-ylethyl]amine, dihydrochloride A mixture of 43.9 mg (0.1 mmol) of tert-butyl[(1R)-1-(2,5-difluorobenzyl)-2-[1,2,4]triazolo[3,4-a]isoquinolin-3-ylethyl]carbamate and 2 mL of 4M HCl in anhydrous dioxane was stirred at room temperature in a stoppered flask. After 2 h, the solvent was evaporated, and the residue was stirred with diethyl ether. The solid was collected on a filter, washed with diethyl ether, and dried to give the title compound as an off-white powder. LC-MS 339 (M+1).

EXAMPLE 5

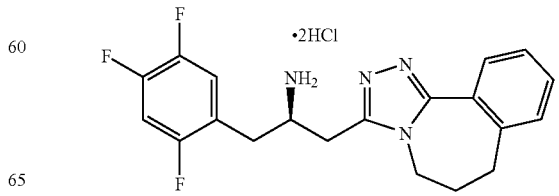

[(1R)-2-(6,7-Dihydro-5H-[1,2,4]triazolo[3,4-a][2]benzazepin-3-yl)-1-(2,4,5-trifluorobenzyl)ethyl]amine dihydrochloride Step A: tert-Butyl [(1R)-2-(6,7-dihydro-5H-[1,2,4]triazolo[3,4-a][2]benzazepin-3-yl)-1-(2,4,5-trifluorobenzyl)ethyl]carbamate A mixture of 90 mg (0.26 mmol) of tert-butyl [(1R)-3-hydrazino-3-oxo-1-(2,4,5-trifluorobenzyl)propyl]carbamate (Intermediate 4), 45.5 mg (0.26 mmol) of 1-methoxy-4,5-dihydro-3H-2-benzazepine (Intermediate 10), and 3.5 mL of 2-methoxyethanol was stirred at reflux for 43 h. The cooled solution was concentrated, and the residue was purified by preparative HPLC (C18 reverse phase column, 20-90% acetonitrile in water containing 0.05% trifluoroacetic acid) to give the title compound as a colorless oil. LC-MS 473 (M+1).

Step B: [(1R)-2-(6,7-Dihydro-5H-[1,2,4]triazolo[3,4-a][2]benzazepin-3-yl)-1-(2,4,5-trifluorobenzyl)ethyl]amine, dihydrochloride The title compound was prepared according to the procedure for Example 1, Step C, to yield the title compound as a pale yellow solid. LC-MS 373 (M+1).

EXAMPLE 6

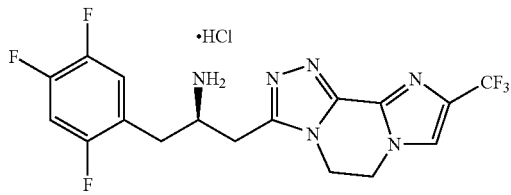

{(1R)-1-(2,4,5-Trifluorobenzyl)-2-[9-(trifluoromethyl)-5,6-dihydroimidazo[1,2-a][1,2,4]triazolo[3,4-c]pyrazin-3-yl]ethyl}amine, hydrochloride Step A: tert-Butyl{(1R)-1-(2,4,5-trifluorobenzyl)-2-[9-(trifluoromethyl)-5,6-dihydroimidazo[1,2-a][1,2,4]triazolo[3,4-c]pyrazin-3-yl]ethyl}carbamate A mixture of 129 mg (0.475 mmol) of tert-butyl[(1R)-3-hydrazino-3-oxo-1-(2,4,5-trifluorobenzyl)propyl]carbamate (Intermediate 4), 129 mg (0.583 mmol) of 2-(trifluoromethyl)-6,7-dihydroimidazo[1,2-a]pyrazine-8(5H)-thione (Intermediate 11), and 8.5 mL of 2-methoxyethanol was stirred at reflux for 3 days. The cooled solution was concentrated, and the residue was purified by preparative HPLC (C18 reverse phase column, 20-90% acetonitrile in water containing 0.05% trifluoroacetic acid) to give the title compound as an oil. LC-MS 517 (M+1).

Step B: {(1R)-1-(2,4,5-Trifluorobenzyl)-2-[9-(trifluoromethyl)-5,6-dihydroimidazo[1,2-a][1,2,4]triazolo[3,4-c]pyrazin-3-yl]ethyl}amine, hydrochloride The title compound was prepared according to the procedure for Example 1, Step C, to yield the title compound as a pale yellow solid. LC-MS 417 (M+1).

EXAMPLE 7

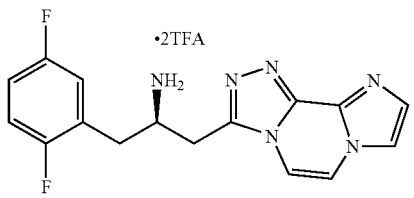

[(1R)-1-(2,5-Difluorobenzyl)-2-imidazo[1,2-a][1,2,4]triazolo[3,4-c]pyrazin-3-ylethyl]amine, bis(trifluoroacetic acid) salt A mixture of 50 mg (0.15 mmol) of tert-butyl[(1R)-1-(2,5-difluorobenzyl)-3-hydrazino-3-oxopropyl]carbamate (Intermediate 2), 28 mg (0.18 mmol) of 8-chloroimidazo[1,2-a]pyrazine (Intermediate 16), and 2.5 mL of 2-methoxyethanol was stirred at reflux for 43 h, resulting primarily in ring closure of the initial adduct as well as loss of the Boc group. The cooled solution was concentrated, and the residue was purified by preparative HPLC (C18 reverse phase column, 0-50% acetonitrile in water containing 0.05% trifluoroacetic acid) to give the title compound as a yellow solid. LC-MS 329 (M+1).

EXAMPLE 8

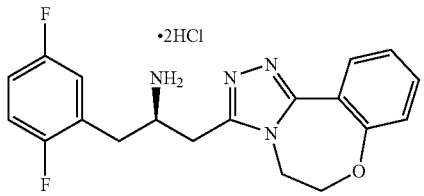

[(1R)-1-(2,5-Difluorobenzyl)-2-(5,6-dihydro[1,2,4]triazolo[4,3-d][1,4]benzoxazepin-3-yl)ethyl]amine, dihydrochloride Step A: tert-butyl[(1R)-2-(10-chloro-5,6-dihydro[1,2,4]triazolo[4,3-d][1,4]benzoxazepin-3-yl)-1-(2,5-difluorobenzyl)ethyl]carbamate By the procedure of Example 5, Step A, the title compound was prepared from tert-butyl[(1R)-1-(2,5-difluorobenzyl)-3-hydrazino-3-oxopropyl]carbamate (Intermediate 2) and 7-chloro-5-methoxy2,3-dihydro-1,4-benzoxazepine (Intermediate 15). LC-MS 491 (M+1).

Step B: tert-Butyl[(1R)-1-(2,5-difluorobenzyl)-2-(5, 6-dihydro[1,2,4]triazolo[4,3-d][1,4]benzoxazepin-3-yl)ethyl]carbamate A mixture of 20 mg (0.0407 mmol) of tert-butyl[(1R)-2-(10-chloro-5,6-dihydro[1,2,4]triazolo[4,3-d][1,4]benzoxazepin-3-yl)-1-(2,5-difluorobenzyl)ethyl]carbamate, 0.007 mL (5.1 mg, 0.05 mmol) of triethylamine, 9.3 mg of 10% palladium on carbon, and 0.5 mL of methanol was shaken with hydrogen (45 psig) for 3 h. The catalyst was removed by filtration, and the filtrate was concentrated to yield the title compound. LC-MS 457 (M+1).

Step C: [(1R)-1-(2,5-Difluorobenzyl)-2-(5,6-dihydro [1,2,4]triazolo[4,3-d][1,4]benzoxazepin-3-yl)ethyl] amine, dihydrochloride By the procedure of Example 1, Step C, tert-butyl[(1R)-1-(2,5-difluorobenzyl)-2-(5,6-dihydro[1,2,4]triazolo[4,3-d][1, 4]benzoxazepin-3-yl)ethyl]carbamate was converted to the title compound. LC-MS 457 (M+1).

EXAMPLE 9

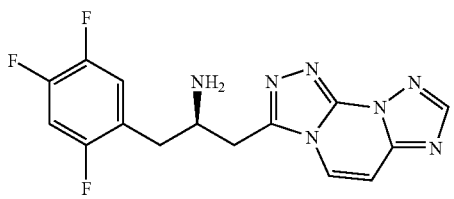

[(1R)-2-Bis[1,2,4]triazolo[1,5-c:4',3'-a]pyrimidin-3-yl-1-(2,4,5-trifluorobenzyl)ethyl]amine Step A: tert-Butyl[(1R)-3-oxo-3-(2-[1,2,4]triazolo[1, 5-c]pyrimidin-5-ylhydrazino)-1-(2,4,5-trifluorobenzyl)propyl]carbamate A solution of 133 mg (0.4 mmol) of (3R)-3-[(tert-butoxycarbonyl)amino]-4-(2,4,5-trifluorophenyl)butanoic acid (Intermediate 3), 84.5 mg (0.44 mmol) of 1-(3-dimethylaminopropyl)-3-ethylcarbodiimide hydrochloride (EDC) and 71 mg (0.5 mmol based on 95% purity) of 1-hydroxybenzotriazole (HOBT) in 1.5 mL of anhydrous DMF was stirred at room temperature in a stoppered flask. After 15 min, this solution was added dropwise by syringe through a septum to a stirred suspension of 72.1 mg (0.48 mmol) of 5-hydrazino [1,2,4]triazolo[1,5-c]pyrimidine (Intermediate 20) 0.209 mL (155 mg, 1.2 mmol) of N,N-diisopropylethylamine in 1 mL of anhydrous DMF. Stirring under nitrogen was continued for 17 h. The mixture was then filtered and concentrated under vacuum. The residue was partitioned between ethyl acetate and 5% aqueous citric acid solution. The organic phase was washed with more 5% citric acid, then with water, and finally with saturated aqueous sodium carbonate solution. The organic solution was dried over magnesium sulfate, filtered and concentrated to yield the title compound as an off-white solid, mp 207.5-209.5° C. LC-MS 488 (M+Na), 366 (M+1-Boc).

Step B: N-[(1R)-2-Bis [1,2,4]triazolo[1,5-c:4',3'-a] pyrimidin-3-yl-1-(2,4,5-trifluorobenzyl)ethyl]acetamide A solution of 93.1 mg (0.2 mmol) of tert-butyl[(1R)-3-oxo-3-(2-[1,2,4]triazolo[1,5-c]pyrimidin-5-ylhydrazino)-1-(2,4, 5-trifluorobenzyl)propyl]carbamate in 10 mL of glacial acetic acid was stirred at reflux under nitrogen for 40 h. The cooled solution was concentrated, and the residue was partitioned between 5 mL of ethyl acetate and 3 mL of saturated sodium carbonate aqueous solution. The organic phase was dried over magnesium sulfate, filtered, and concentrated to dryness. The residue was purified by preparative thin-layer chromatography on silica gel (92.5:7.5 dichloromethane:methanol), giving the title compound as a white solid, mp 233-235° C. LC-MS 390 (M+1).

Step C: [(1R)-2-Bis[1,2,4]triazolo[1,5-c:4',3'-a]pyrimidin-3-yl-1-(2,4,5-trifluorobenzyl)ethyl]amine A solution of 26.1 mg (0.067 mmol) of N-[(1R)-2-bis[1,2, 4]triazolo[1,5-c:4',3'-a]pyrimidin-3-yl-1-(2,4,5-trifluorobenzyl)ethyl]acetamide in 3 mL of 6N hydrochloric acid was stirred at reflux under nitrogen for 12 h. The solution was evaporated to dryness, and the residue was purified by preparative thin-layer chromatography on silica gel (90:10:1 dichloromethane:methanol:concentrated ammonium hydroxide) to give the title compound as a white solid. LC-MS 348 (M+1).

EXAMPLE 10

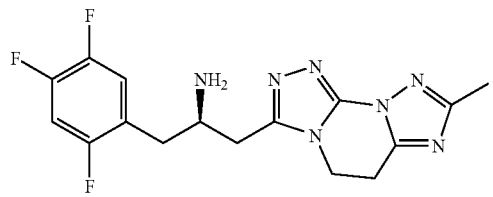

[(1R)-2-(8-Methyl-5,6-dihydrobis[1,2,4]triazolo[1,5-c:4',3'-a]pyrimidin-3-yl)-1-(2,4,5-trifluorobenzyl) ethyl]amine Step A: tert-Butyl[(1R)-3-[2-(2-methyl-7,8-dihydro [1,2,4]triazolo[1,5-c]pyrimidin-5-yl)hydrazino]-3-oxo-1-(2,4,5-trifluorobenzyl)propyl]carbamate A solution of 139 mg (0.4 mmol) of tert-butyl[(1R)-3-hydrazino-3-oxo-1-(2,4,5-trifluorobenzyl)propyl]carbamate (Intermediate 4) and 72.9 mg (0.4 mmol) of 2-methyl-5-(methylthio)-7,8-dihydro[1,2,4]triazolo[1,5-c]pyrimidine (Intermediate 30) in 5 mL of 1-butanol was stirred at reflux for 76 h. The cooled solution was concentrated, and the residue containing the title compound was used directly in the next step. LC-MS 482 (M+1).

Step B: N-[(1R)-2-(8-Methyl-5,6-dihydrobis[1,2,4] triazolo[1,5-c:4',3'-a]pyrimidin-3-yl)-1-(2,4,5-trifluorobenzyl)ethyl]acetamide The crude residue from Step A was dissolved in 5 mL of glacial acetic acid, and the resulting solution was stirred at reflux for 60 h. The cooled solution was concentrated, and the residue was partitioned between 1:1 ethyl acetate:tetrahydrofuran and saturated sodium carbonate aqueous solution. The organic phase was dried over magnesium sulfate, filtered, and concentrated to dryness. Purification of the residue by preparative thin-layer chromatography on silica gel (three successive developments in 95:5, 92.5:7.5, and 90:10 dichloromethane:methanol) afforded the title compound as a stiff foam. LC-MS 406 (M+1).

Step C: [(1R)-2-(8-Methyl-5,6-dihydrobis[1,2,4]triazolo[1,5-c:4',3'-a]pyrimidin-3-yl)-1-(2,4,5-trifluorobenzyl)ethyl]amine By the procedure of Example 9, Step C (with reaction time shortened to 6 h), N-[(1R)-2-(8-methyl-5,6-dihydrobis[1,2,4]triazolo[1,5-c:4',3'-a]pyrimidin-3-yl)-1-(2,4,5-trifluorobenzyl)ethyl]acetamide was converted to the title compound. LC-MS 364 (M+1).

EXAMPLE 11

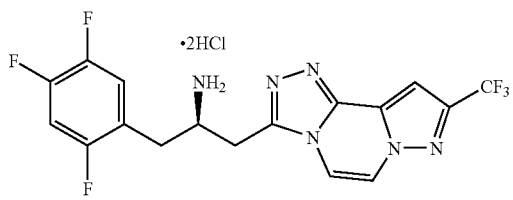

{(1R)-1-(2,4,5-Trifluorobenzyl)-2-[9-(trifluoromethyl)pyrazolo[1,5-a][1,2,4]triazolo[3,4c]pyrazin-3-yl]ethyl}amine, dihydrochloride Step A: tert-Butyl{(1R)-1-(2,4,5-trifluorobenzyl)-2-[9-(trifluoromethyl)pyrazolo[1,5-a][1,2,4]triazolo[3,4-c]pyrazin-3-yl]ethyl}carbamate A mixture of 7.7 mg (0.22 mmol) of tert-butyl[(1R)-3-hydrazino-3-oxo-1-(2,4,5-trifluorobenzyl)propyl]carbamate (Intermediate 4), 4.9 mg (0.22 mmol) of 4-chloro-2-(trifluoromethyl)pyrazolo[1,5-a]pyrazine (Intermediate 39), and 0.5 mL of xylenes was stirred at reflux for 19 h. The cooled solution was concentrated to yield the title compound, sufficiently pure for use in the next step. LC-MS 515 (M+1).

Step B: {(1R)-1-(2,4,5-Trifluorobenzyl)-2-[9-(trifluoromethyl)pyrazolo[1,5-a][1,2,4]triazolo[3,4-c]pyrazin-3-yl]ethyl}amine, dihydrochloride By the procedure of Example 1, Step C, the title compound was obtained from tert-butyl{(1R)-1-(2,4,5-trifluorobenzyl)-2-[9-(trifluoromethyl)pyrazolo[1,5-a][1,2,4]triazolo[3,4c]-pyrazin-3-yl]ethyl}carbamate as a white solid. LC-MS 415 (M+1).

EXAMPLE 12

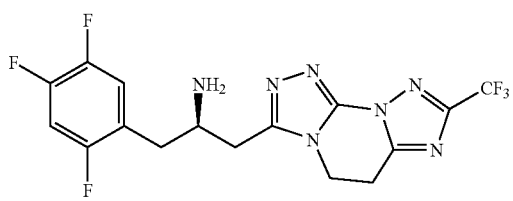

{(1R)-1-(2,4,5-Trifluorobenzyl)-2-[8-(trifluoromethyl)-5,6-dihydrobis[1,2,4]triazolo[1,5-c:4',3'-a]pyrimidin-3-yl]ethyl}amine Step A: tert-Butyl((1R)-3-oxo-1-(2,4,5-trifluorobenzyl)-3-{2-[2-(trifluoromethyl)-[1,2,4]triazolo[1,5-c]pyrimidin-5-yl]hydrazino}propyl)carbamate By the procedure of Example 9, Step A, 5-hydrazino-2-(trifluoromethyl)[1,2,4]triazolo[1,5-c]pyrimidine (Intermediate 42) was acylated with (3R)-3-[(tert-butoxycarbonyl)amino]-4-(2,4,5-trifluorophenyl)butanoic acid (Intermediate 3). Purification by flash chromatography on silica gel (1-5% methanol in dichloromethane) afforded the title compound as a light tan solid, mp 159-161° C. LC-MS 534 (M+1).

Step B: N-{(1R)-1-(2,4,5-Trifluorobenzyl)-2-[8-(trifluoromethyl)bis[1,2,4]triazolo[1,5-c:4',3'-a]pyrimidin-3-yl]ethyl}acetamide The procedure of Example 9, Step B, was applied to tert-butyl((1R)-3-oxo-1-(2,4,5-trifluorobenzyl)-3-{2-[2-(trifluoromethyl)[1,2,4]triazolo[1,5-c]pyrimidin-5-yl]hydrazino}propyl)carbamate. Purification by preparative thin-layer chromatography on silica gel (three successive developments in 95:5 dichloromethane:methanol followed by a final development in 94:6 dichloromethane:methanol) yielded the title compound as an off-white powder. LC-MS 458 (M+1).

Step C: N-{(1R)-1-(2,4,5-Trifluorobenzyl)-2-[8-(trifluoromethyl)-5,6-dihydrobis[1,2,4]triazolo[1,5-c:4',3'-a]pyrimidin-3-yl]ethyl}acetamide A mixture of 52.1 mg (0.114 mmol) of N-{(1R)-1-(2,4,5-trifluorobenzyl)-2-[8-(trifluoromethyl)bis[1,2,4]triazolo[1,5-c:4',3'-a]pyrimidin-3-yl]ethyl}acetamide, 52 mg of 10% palladium on carbon, and 5 mL of 2-methoxyethanol was shaken with hydrogen (52 psi) for 26 h. The catalyst was removed by filtration through Celite, and the filtrate was concentrated to dryness. The residue was purified by preparative thin-layer chromatography on silica gel (three successive developments in 92.5:7.5 dichloromethane:methanol) to provide the title compound. LC-MS 460 (M+1).

Step D: {(1R)-1-(2,4,5-Trifluorobenzyl)-2-[8-(trifluoromethyl)-5,6-dihydrobis[1,2,4]triazolo[1,5-c:4',3'-a]pyrimidin-3-yl]ethyl}amine The title compound was obtained from N-{(1R)-1-(2,4,5-trifluorobenzyl)-2-[8-trifluoromethyl)-5,6-dihydrobis[1,2,4]triazolo[1,5-c:4',3'-a]pyrimidin-3-yl]ethyl}acetamide accord the procedure of Example 9, Step C. LC-MS 418 (M+1).

Essentially following the procedures outlined for Examples 1-12, the compounds listed in Tables 2 and 3 were prepared from the intermediates described herein.

TABLE 1
| Example | R³ | D—E—A | L—M | MS (M + 1) |
|---|---|---|---|---|
| 13 | 2-F,4-F,5-F | —CH₂—CH₂— | 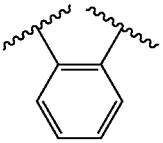 | 359 |
| 14 | 2-F,5-F | —CH₂—CH₂—S— | 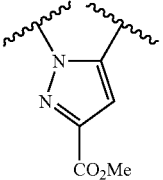 | 373 |
| 15 | 2-F,5-F | —CH₂—CH₂—CH₂— | 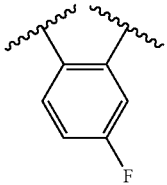 | 403 |
| 16 | 2-F,5-F | —CH₂—CH₂—O— | 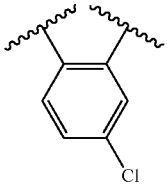 | 375 |
| 17 | 2-F,5-F | —CH₂—CH₂—O— | 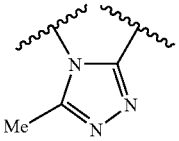 | 391 |
| 18 | 2-F,4-F,5-F | —CH=CH— | 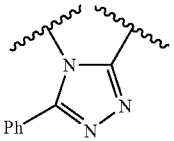 | 362 |
| 19 | 2-F,4-F,5-F | —CH=CH— | 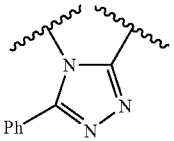 | 424 |

TABLE 1-continued

| Example | R³ | D—E—A | L—M | MS (M + 1) |
|---|---|---|---|---|
| 20 | 2-F,4-F,5-F | —CH=CH— | 1,2,4-triazole (N1,C3-linked) | 348 |
| 21 | 2-F,4-F,5-F | —CH=CH— | pyrazine with Ph and CF₃ | 503 |
| 22 | 2-F,4-F,5-F | —CH=CH— | pyrazine with F₃C and Ph | 503 |
| 23 | 2-F,4-F,5-F | —CH=CH— | 1,2,4-triazole (N1,C5-linked) | 348 |
| 24 | 2-F,4-F,5-F | —CH=CH— | pyrazine with Me | 373 |
| 25 | 2-F,4-F,5-F | —CH=CH— | pyrazine with Me | 373 |
| 26 | 2-F,4-F,5-F | —CH=CH— | pyrazine with Ph | 435 |

TABLE 1-continued
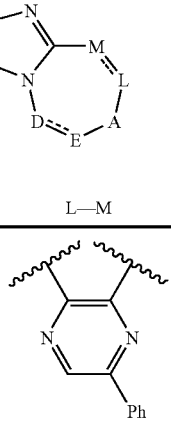
| Example | R³ | D—E—A | L—M | MS (M + 1) |
|---|---|---|---|---|
| 27 | 2-F,4-F,5-F | —CH=CH— | 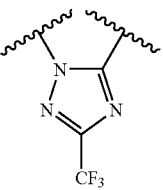 | 435 |
| 28 | 2-F,4-F,5-F | —CH=CH— | 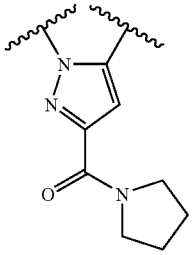 | 416 |
| 29 | 2-F,4-F,5-F | —CH₂—CH₂—CH₂— | 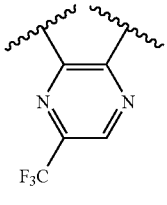 | 460 |
| 30 | 2-F,4-F,5-F | —CH=CH— | 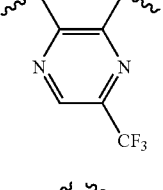 | 427 |
| 31 | 2-F,4-F,5-F | —CH=CH— | 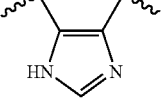 | 427 |
| 32 | 2-F,4-F,5-F | —CH=CH— | 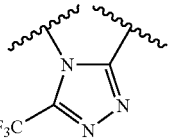 | 370 (M + Na) |
| 33 | 2-F,4-F,5-F | —CH=CH— |  | 416 |

TABLE 1-continued
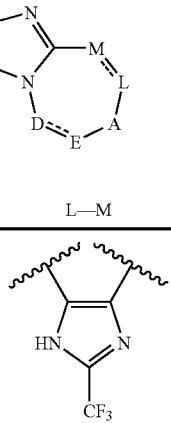
| Example | R³ | D—E—A | L—M | MS (M + 1) |
|---|---|---|---|---|
| 34 | 2-F,4-F,5-F | —CH=CH— | 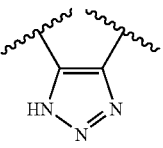 | 415 |
| 35 | 2-F,4-F,5-F | —CH=CH— | 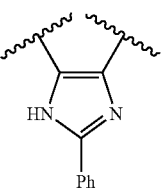 | 348 |
| 36 | 2-F,4-F,5-F | —CH=CH— | 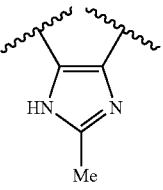 | 423 |
| 37 | 2-F,4-F,5-F | —CH=CH— | 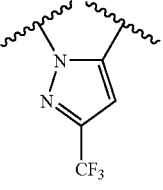 | 361 |
| 38 | 2-F,4-F,5-F | —CH₂—CH₂—CH₂— | 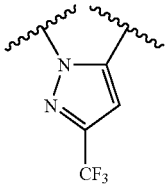 | 431 |
| 39 | 2-F,4-F,5-F | —CH₂—CH₂— | | 417 |
| 40 | 2-F,4-F,5-F | —CH=CH— | 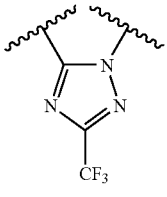 | 416 |

TABLE 1-continued

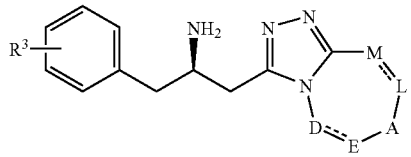

| Example | R³ | D—E—A | L—M | MS (M + 1) |
|---|---|---|---|---|
| 41 | 2-F,4-F,5-F | —CH=CH— | 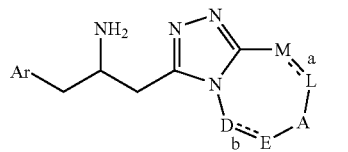 | 424 |

EXAMPLE OF A PHARMACEUTICAL FORMULATION

As a specific embodiment of an oral pharmaceutical composition, a 100 mg potency tablet is composed of 100 mg of Example 1, Example 2, or Example 12, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

(I)

or a pharmaceutically acceptable salt thereof; wherein
"a" and "b" represent single or double bonds;
Ar is phenyl, which is unsubstituted or substituted with one to five R³ substituents;
each R³ is independently selected from the group consisting of:

(1) halogen,
(2) $C_{1-6}$ alkyl, which is unsubstituted or substituted with one to five halogens,
(3) $C_{1-6}$ alkoxy, which is unsubstituted or substituted with one to five halogens,
(4) CN, and
(5) hydroxyl;

A is $CH_2$, O, S, or a single bond;

D-E together are —$CH_2CH_2$— or —CH=CH—, when A is a single bond; or —$CH_2CH_2$— when A is $CH_2$, O, or S;

L-M together represents a fused ring selected from the group consisting of:

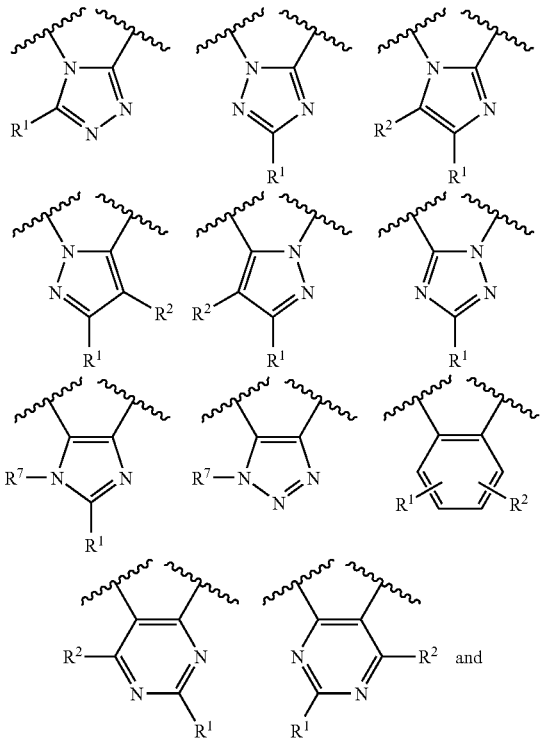

-continued

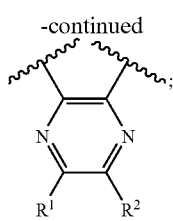

$R^1$ and $R^2$ are each independently selected from the group consisting of:
(1) hydrogen,
(2) $C_{1-10}$ alkyl, which is unsubstituted or substituted with:
  (a) one to five halogens or
  (b) phenyl, which is unsubstituted or substituted with one to five substituents independently selected from halogen, CN, OH, $R^4$, $OR^4$, $NHSO_2R^4$, $N(C_{1-6}$ alkyl$)SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl which is unsubstituted or substituted with one to five substituents independently selected from halogen, CN, OH, $R^4$, $OR^4$, $NHSO_2R^4$, $N(C_{1-6}$ alkyl$)SO_2R^4$, $SO_2R^4$, $SO_2NR^5R^6$, $NR^5R^6$, $CONR^5R^6$, $CO_2H$, and $CO_2C_{1-6}$ alkyl,
(4) a 5- or 6-membered heterocycle which may be saturated or unsaturated containing one to four heteroatoms independently selected from N, S and O, said heterocycle being unsubstituted or substituted with one to three substituents independently selected from oxo, halogen, $NO_2$, CN, OH, $R^4$, $OR^4$, $NHSO_2R^4$, $N(C_{1-6}$ alkyl$)SO_2R^4$, $SO_2R^4$, $SO_2NR^5R^6$, $NR^5R^6$, $CONR^5R^6$, $CO_2H$, and $CO_2C_{1-6}$ alkyl,
(5) $C_{3-6}$ cycloalkyl, which is unsubstituted or substituted with one to three substituents independently selected from halogen, OH, $C_{1-6}$ alkyl, and $C_{1-6}$ alkoxy, wherein alkyl and alkoxy are optionally substituted with one to five halogens,
(6) OH,
(7) $OR^4$,
(8) $SR^4$,
(9) $SO_2R^4$,
(10) $SO_2NR^5R^6$,
(11) $NR^5R^6$,
(12) CN,
(13) $CO_2H$,
(14) $CO_2C_{1-6}$ alkyl,
(15) $CONR^5R^6$, and
(16) halogen;
$R^4$ is $C_{1-6}$ alkyl, which is unsubstituted or substituted with one to five substituents independently selected from halogen, $CO_2H$, and $CO_2C_{1-6}$ alkyl;
$R^5$ and $R^6$ are each independently selected from the group consisting of:
(1) hydrogen,
(2) phenyl, which is unsubstituted or substituted with one to five substituents independently selected from halogen, OH, $C_{1-6}$ alkyl, and $C_{1-6}$ alkoxy, wherein alkyl and alkoxy are optionally substituted with one to five halogens,
(3) $C_{3-6}$ cycloalkyl, which is unsubstituted or substituted with one to three substituents independently selected from halogen, OH, $C_{1-6}$ alkyl, and $C_{1-6}$ alkoxy, wherein alkyl and alkoxy are optionally substituted with one to five halogens, and
(4) $C_{1-6}$ alkyl, which is unsubstituted or substituted with a substituent selected from the group consisting of:
  (a) one to five halogens,
  (b) OH,
  (c) $C_{1-6}$ alkoxy, and
  (d) phenyl, which is unsubstituted or substituted with one to five substituents independently selected from halogen, OH, $C_{1-6}$ alkyl, and $C_{1-6}$ alkoxy, wherein alkyl and alkoxy are optionally substituted with one to five halogens;
  or $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and
$R^7$ is hydrogen or $C_{1-4}$ alkyl.

2. The compound of claim 1 wherein the carbon atom marked with an * has the R stereochemical configuration as depicted in structural formula Ia:

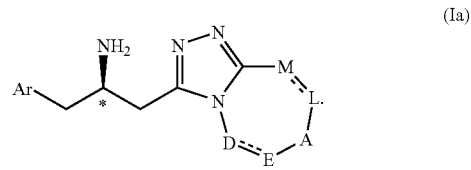

(Ia)

3. The compound of claim 2 of the structural formula Ib:

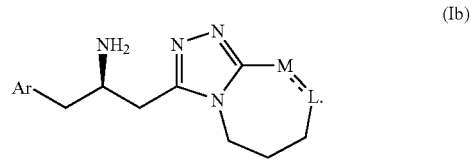

(Ib)

4. The compound of claim 3 of the structural formula Ib2:

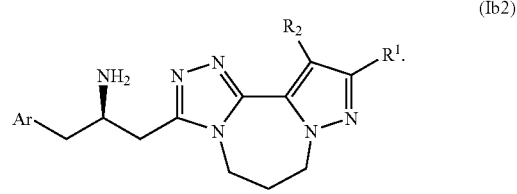

(Ib2)

5. The compound of claim 2 of the structural formula Ie:

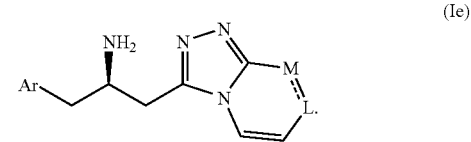

(Ie)

6. The compound of claim 5 of the structural formula Ie3:

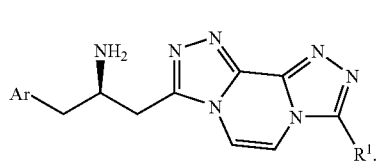
(Ie3)

7. The compound of claim 5 of the structural formula Ie6:

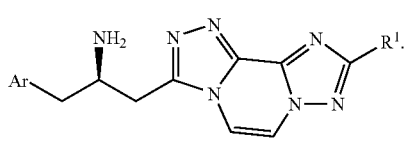
(Ie6)

8. The compound of claim 2 of the structural formula If:

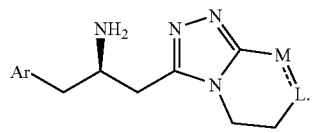
(If)

9. The compound of claim 8 of the structural formula If1:

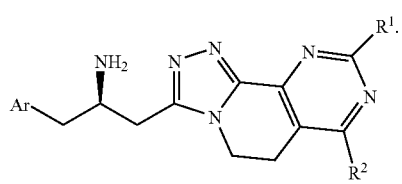
(If1)

10. The compound of claim 8 of the structural formula If2:

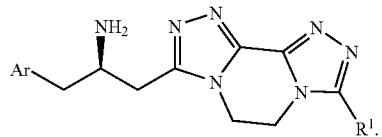
(If2)

11. The compound of claim 8 of the structural formula If4:

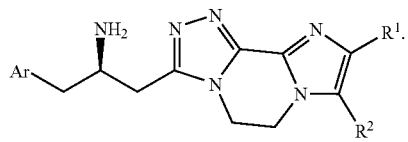
(If4)

12. The compound of claim 8 of the structural formula If5:

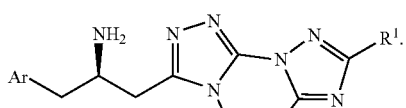
(If5)

13. The compound of claim 8 of the structural formula If6:

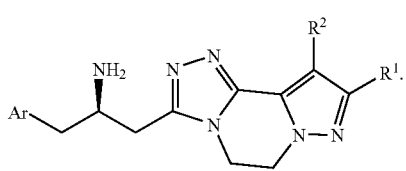
(If6)

14. The compound of claim 8 of the structural formula If7:

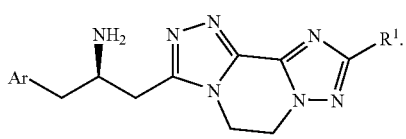
(If7)

15. The compound of claim 1 wherein L-M together represents a fused ring selected from the group consisting of:

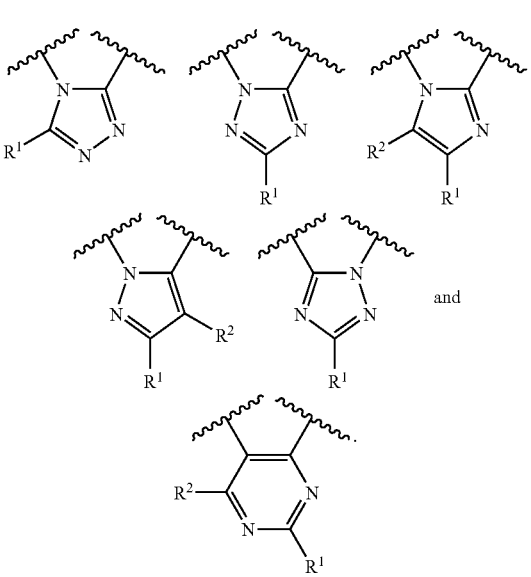

16. The compound of claim 1 wherein Ar is selected from the group consisting of phenyl; 2-fluorophenyl; 3,4-difluorophenyl; 2,5-difluorophenyl; and 2,4,5-trifluorophenyl.

17. The compound of claim 1 wherein $R^1$ and $R^2$ are each independently selected from the group consisting of:
 (1) hydrogen,
 (2) methyl,
 (3) $CF_3$,
 (4) phenyl which is unsubstituted or substituted with one to three fluorines, (5) $C_{o2}C_{1-4}$ alkyl,
(6) $CONR^5R^6$,
(7) fluorine, and
(8) chlorine.

18. The compound of claim 1 wherein $R^5$ and $R^6$ are each independently selected from the group consisting of:
   (1) hydrogen,
   (2) cyclopropyl, and
   (3) $C_{1-4}$ alkyl, which is linear or branched and which is unsubstituted or substituted with fluoro, OH, $C_{1-4}$ alkoxy;
   or wherein $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one or two substituents independently selected from fluoro, hydroxy, Me, and OMe.

19. The compound of claim 1 which is selected from the group consisting of:

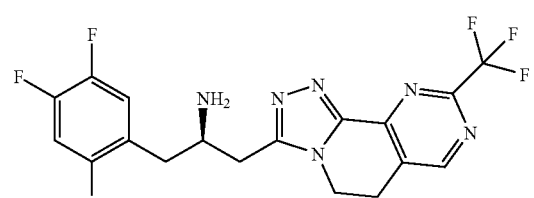

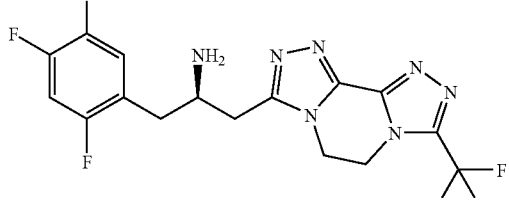

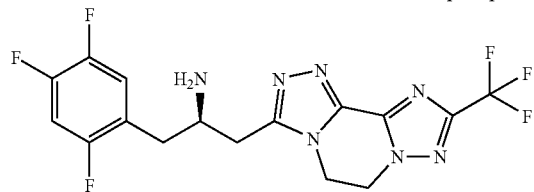

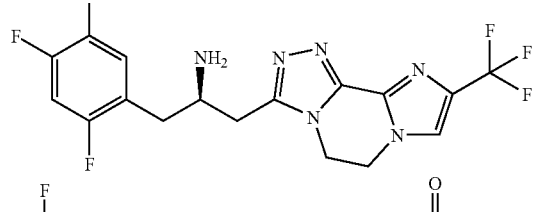

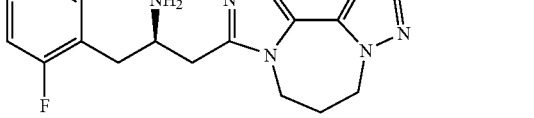

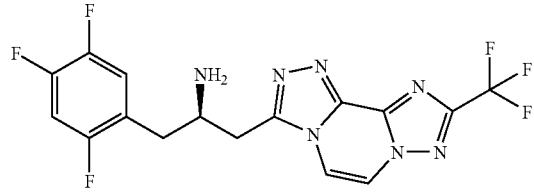

-continued

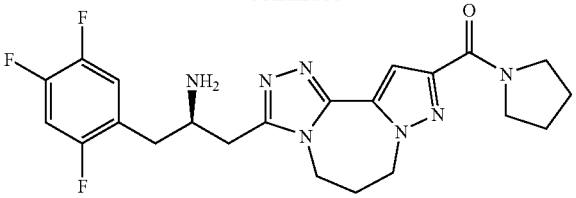

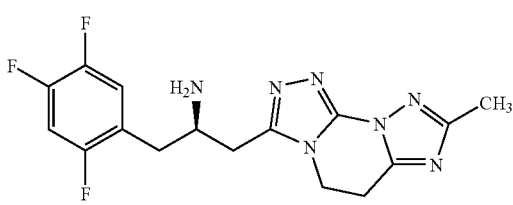

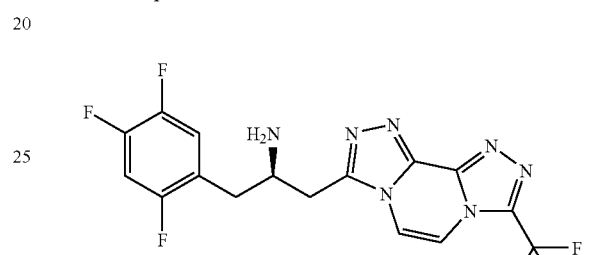

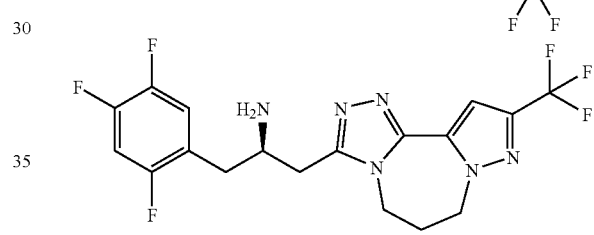

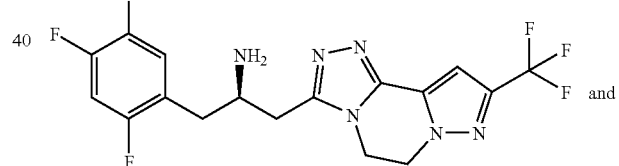

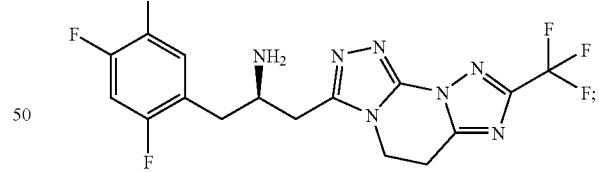

or a pharmaceutically acceptable salt thereof.

20. A pharmaceutical composition which comprises a compound of claim 1 and a pharmaceutically acceptable carrier.

21. The pharmaceutical composition of claim 20 additionally comprising metformin.

22. A method for treating non-insulin dependent (Type 2) diabetes in a mammal in need thereof which comprises the administration to the mammal of a therapeutically effective amount of a compound of claim 1.

* * * * *